United States Patent
Kennedy, II et al.

(10) Patent No.: US 8,002,814 B2
(45) Date of Patent: Aug. 23, 2011

(54) OVER THE ENDOSCOPE INTRODUCER FOR STENTS

(75) Inventors: Kenneth C. Kennedy, II, Clemmons, NC (US); Gregory J. Skerven, Kernersville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/709,888

(22) Filed: Feb. 22, 2010

(65) Prior Publication Data

US 2010/0161024 A1  Jun. 24, 2010

Related U.S. Application Data

(62) Division of application No. 11/604,406, filed on Nov. 27, 2006, now Pat. No. 7,717,923.

(60) Provisional application No. 60/740,900, filed on Nov. 30, 2005.

(51) Int. Cl.
*A61F 2/84* (2006.01)
*A61F 2/06* (2006.01)

(52) U.S. Cl. ............................... 623/1.11; 623/1.23

(58) Field of Classification Search .............. 600/101, 600/104, 106, 121, 127, 129, 153; 604/264; 606/108, 191, 194; 623/1.11–1.12, 1.23
See application file for complete search history.

(56) References Cited

U.S. PATENT DOCUMENTS

| | | | |
|---|---|---|---|
| 5,312,343 A * | 5/1994 | Krog et al. | 604/101.03 |
| 5,562,601 A | 10/1996 | Takada | |
| 5,603,698 A | 2/1997 | Roberts et al. | |
| 6,146,389 A | 11/2000 | Getiz | |
| 6,221,081 B1 | 4/2001 | Mikus et al. | |
| 6,264,689 B1 | 7/2001 | Colgan et al. | |
| 6,576,005 B1 | 6/2003 | Geitz | |
| 2002/0161341 A1 | 10/2002 | Stinson et al. | |
| 2005/0033402 A1* | 2/2005 | Cully et al. | 623/1.11 |
| 2005/0033403 A1 | 2/2005 | Ward et al. | |

FOREIGN PATENT DOCUMENTS

| | | |
|---|---|---|
| DE | 10004979 A1 | 8/2000 |
| GB | 2348138 A | 9/2000 |
| WO | WO 99/53865 | 10/1999 |
| WO | WO 2004/030571 | 4/2004 |

OTHER PUBLICATIONS

International Search Report and Written Opinion dated Mar. 21, 2007, for International Application No. PCT/US2006/045422.
Office Action issued in Canadian Application No. 2,632,051 on Dec. 21, 2009.

* cited by examiner

*Primary Examiner* — Anhtuan T Nguyen
*Assistant Examiner* — Ashley Cronin
(74) *Attorney, Agent, or Firm* — Brinks Hofer Gilson & Lione

(57) ABSTRACT

Over-the-scope stent introducers for detachably engaging at least a portion of the outside of an endoscope insert and for delivering a stent are provided. Embodiments include an inner member having a distal first end portion and a proximal second end portion and openings defining a channel. The inner member includes an outer surface, inner endoscope engaging surface, and stent abutting restraint disposed at the first end portion. Embodiments also include an outer member having a distal section and proximal section having openings defining a passageway sized to slideably receive at least a portion of the inner member, and a stent carrying inner chamber disposed at the distal section passageway and being configured to releasably contain a stent. In alternative embodiments, the inner and outer members are elongated to dispose substantially concentrically over a majority of an endoscope insert.

15 Claims, 16 Drawing Sheets

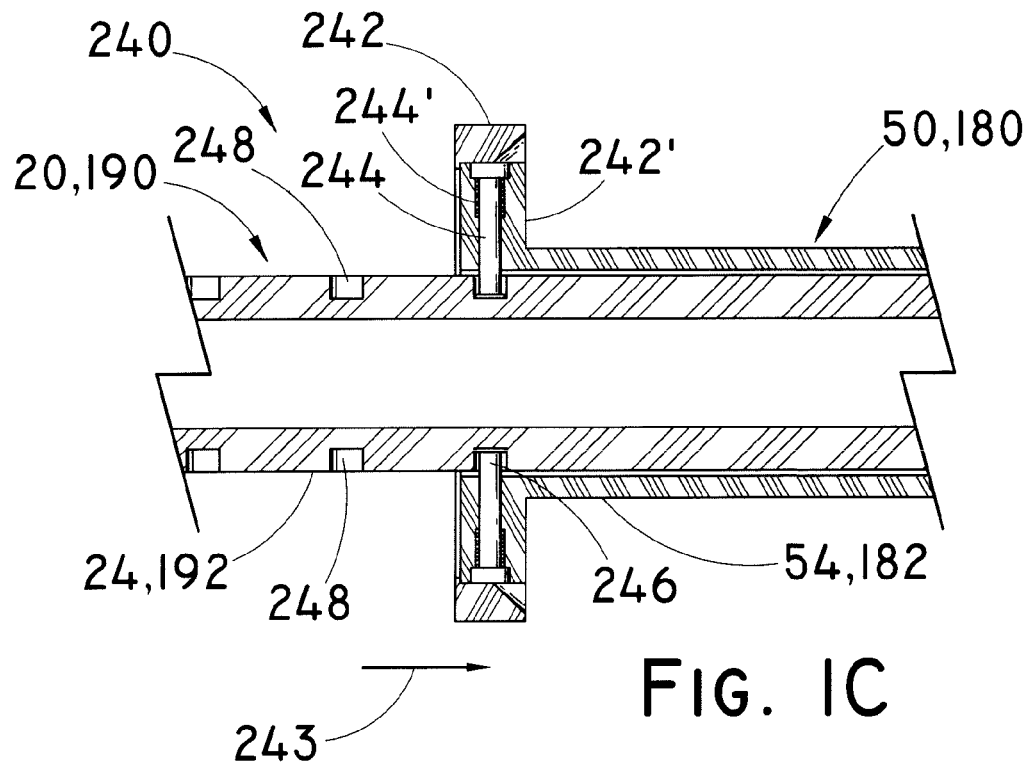
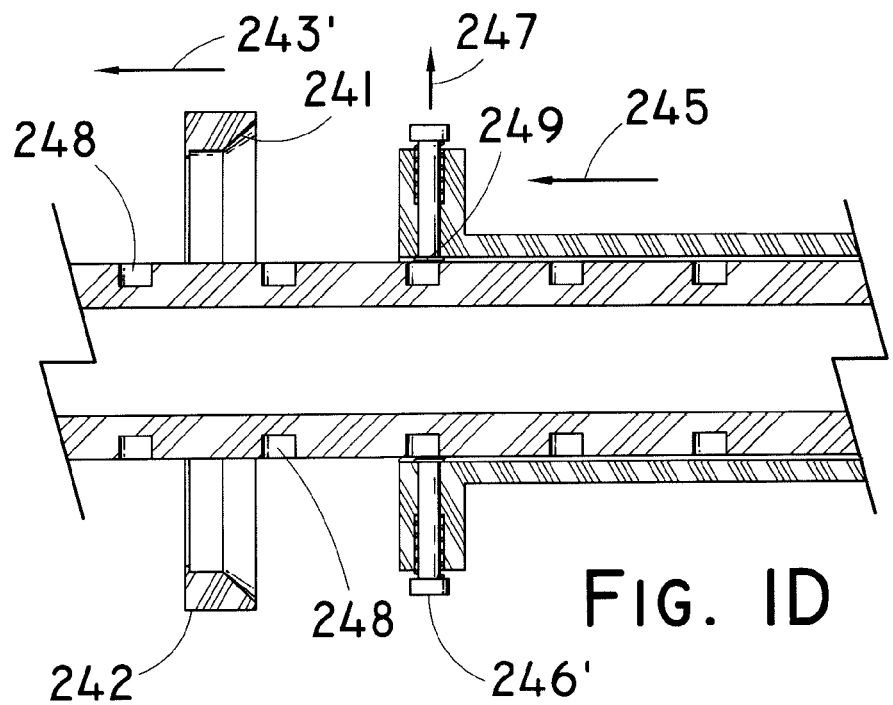

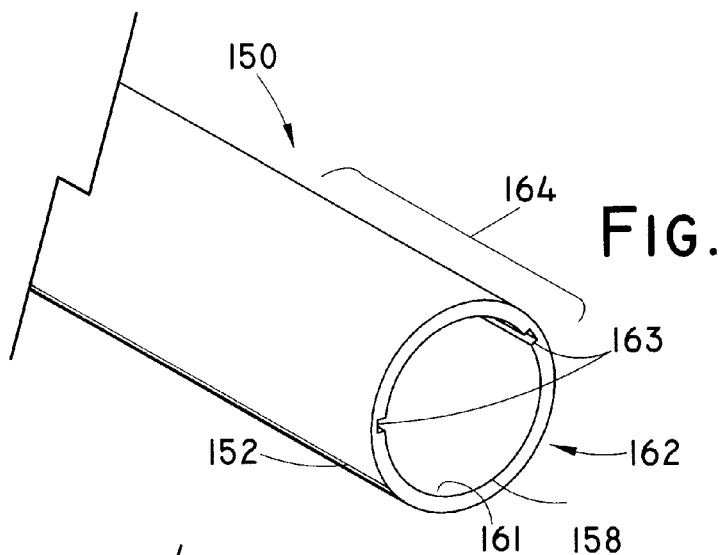
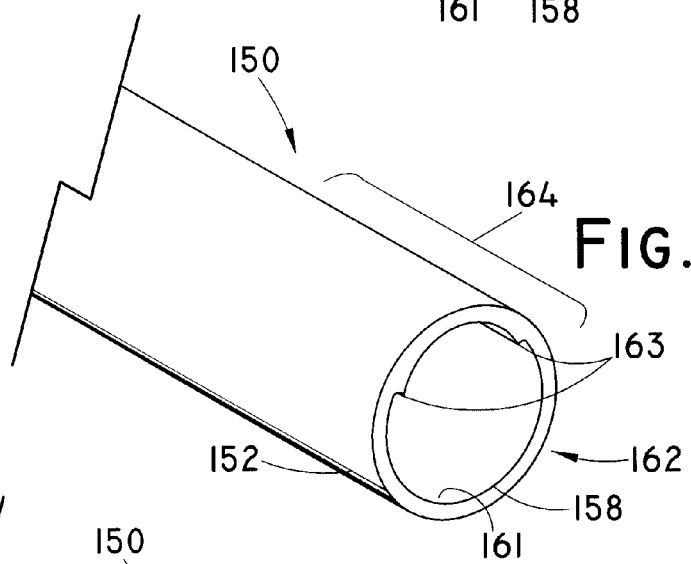
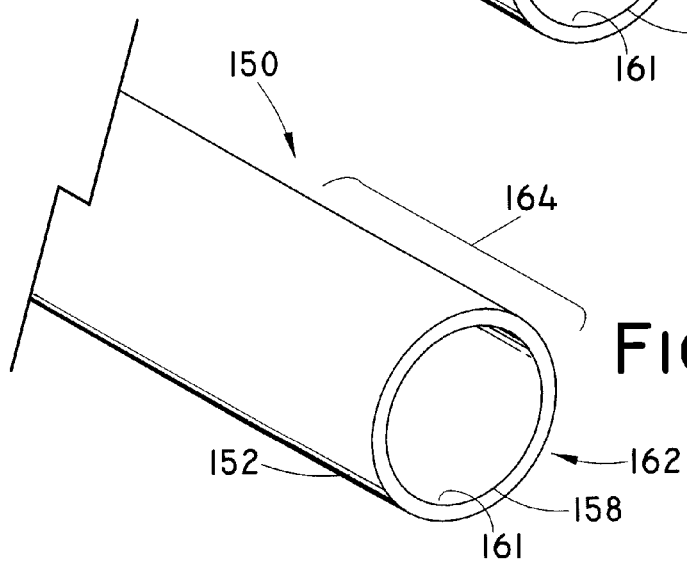

OVER THE ENDOSCOPE INTRODUCER FOR STENTS

RELATED APPLICATIONS

This application is a divisional application of commonly-assigned U.S. patent application Ser. No. 11/604,406, now U.S. Pat. No. 7,717,923 filed on Nov. 27, 2006 that claims the benefit of the filing date under 35 U.S.C. §119(e) of the United States Provisional Patent Application filed on Nov. 30, 2005 entitled, "Over the Endoscope Introducer for Stents," and having an application Ser. No. 60/740,900, the disclosures of which are hereby incorporated by reference in their entirety. Specific reference to U.S. patent application Ser. No. 11/604,406 and provisional application Ser. No. 60/740,900 is made in accordance with 35 U.S.C. §120.

FIELD OF THE INVENTION

The present invention relates to stent introducers that can be used over an endoscope, and methods of using those devices.

BACKGROUND OF THE INVENTION

Placing self-expanding metallic, polymeric, and plastic stents or non-expanding metallic, polymeric, and plastic stents at target sites in the gastrointestinal tract and colon provides easy, safe, and effective palliation of malignant obstructions and other strictures. Indeed, where the disease in the patient becomes inoperable due to tumor extension, distant metastasis, debilitating condition, or advanced age, stents provide the better palliative treatment relative to a removable plastic tube or a removable plastic medical device intended for locations in a body.

Conventional delivery systems allow placement of stents through an endoscope working channel, beside an endoscope through a channel of an endoscope accessory device, or blind (i.e. without an endoscope). The problem is that the stent may be too large to be placed through these channels. The present invention provides, however, an alternative delivery system for the delivery of larger stents (e.g., colonic, pyloric, and the like)—where the stent is too large to be placed through the endoscope or endoscope working channel. Because the present invention works with an endoscope, it further has an advantage over placing the stent blindly.

Endoscopes

Endoscopic surgery has seen rapid growth over the past decade. A wide range of applications have been developed for the general field of endoscopes. Several applications include, by way of example only, some endoscopes that are rigid and other endoscopes that are flexible: arthroscope, angioscope, bronchoscope, choledochoscope, colonoscope, cytoscope, duodenoscope, enteroscope, esophagogastro-duodenoscope (gastroscope), laparoscope, laryngoscope, nasopharyngoneproscope, sigmoidoscope, thoracoscope, and utererscope (individually and collectively, "endoscope").

By way of background, a conventional endoscope has a proximal control section and, extending distally therefrom, a distal insertion portion. The terms "endoscope insert" and "insert" shall include the distal insertion portion to be inserted into a patient, whether that distal insertion portion is part of a rigid endoscope or is the elongate (long) flexible tubular section of a flexible endoscope. In addition, the terms "endoscope insert" and "insert" include any medical device such as a sheath, for example, that might be mounted onto the rigid or flexible distal insertion portion to be inserted into a patient. As is conventional, the term "distal" means away from the physician, operator, or healthcare professional (collectively, "physician") when the device is inserted into a patient, while the term "proximal" means closest to or toward the physician or operator when the device is inserted into a patient.

The proximal control section remains outside the patient during a medical procedure and has several common features. One such feature includes a means for viewing the scene through a viewing lens disposed at the distal working insertion portion of the elongate tubular section. Other common features include a working channel for passing a tool, a light guide cable, and a power supply. For endoscopes of the flexible type, another feature may be one or more (often a pair) of articulation control knobs located at the proximal control section outside the patient for manipulating (bending and articulating) the position of the flexible distal insertion portion inside the patient's body—often, most of the flexible distal insertion portion is passively flexible, while the distal 10.0-20.0 millimeters is flexibly controlled by the articulation knobs.

The conventional endoscope further includes a light source and an image sensor for visualizing the interior of an internal region of a body. In order to form an image of the scene under observation, the light source and image sensor are located at or near the flexible distal insertion end portion of the elongate tubular section of the endoscope to be inserted into a body cavity of a patient.

The overall length and diameter of the tubular section of the endoscope may vary depending on the intended application for the endoscope. By way of example only and not by way of limitation, one embodiment according to the present invention may fit any endoscope, such as any variety of pediatric endoscope, having an outer diameter as small as approximately 5.0 millimeters. In addition, embodiments may be utilized with many sizes of endoscopes. For instance, a standard colonoscope for insertion into the colon and distal terminal ileum typically measures approximately from approximately 1,330 millimeters ("mm") to approximately 1,850 mm in length and from about 11.1 mm to about 19 mm in diameter. The esophagogastroduodenoscope (the "gastroscope") used for insertion into the esophagus, stomach, and duodenum may have an insertion tube with a working length that measures approximately a meter, from about 925 mm to about 1,100 mm in length, and an insertion tube diameter from approximately 5.1 mm to about 12.8 mm. An example of a longer type of endoscope is the enteroscope for insertion into the duodenum and proximal portion of the jejunum. The enteroscope may have an insertion tube that measures over 2 meters in length, from about 2,180 mm to about 2,800 mm, and an insertion tube diameter from approximately 5 mm to about 11.7 mm. A standard duodenoscope for endoscopic retrograde cholangio-pancreatography typically includes an insertion tube from about 1,030 mm to about 1,250 mm in length and from approximately 7.4 to approximately 12.6 mm in diameter. A standard choledoschoscope for passing through the channel of a duodenoscope or inserting intraductally for the bile and pancreatic ducts has an insertion tube length from about 1,870 mm to about 1,900 mm and an insertion tube diameter from approximately 2.8 mm to approximately 3.4 mm. An echoendoscope for the luminal digestive tract and adjacent organs may have an insertion tube length from about 975 mm to about 1,325 mm and an insertion tube diameter from approximately 7.9 mm to approximately 13.7 mm. An example of a shorter type of endoscope is the sigmoidoscope for the rectum and sigmoid colon. The sigmoidoscope may include an insertion tube that measures from about 630 mm to about 790 mm in length and a diameter from approximately 12.2 mm to approximately 13.3 mm.

Endoscopes may also incorporate additional functionality for observation or operation within the body, such as a working channel having an opening located at the distal end portion of the insert. Similar to the variable lengths and diameters of the different types of endoscopes, the working channels vary in diameter: gastroscope (≈2.0-6.0 mm); enteroscope (≈1.0-3.5 mm); duodenoscope (≈2.0-4.8 mm); choledochoscope (≈0.75-1.2 mm); echoendoscope (≈2.2-3.7 mm); colonoscope (≈2.8-4.2 mm); and sigmoidoscope (≈3.2-4.2 mm).

Through this working channel, the physician may pass diagnostic, monitoring, treating, or surgical tools to a site external to the distal end face of the flexible distal insertion end portion of the elongate tubular endoscope and into the observation field and working space of the physician's endoscope. For instance, stent delivery systems may be introduced through the endoscope working channel.

Stents

Minimally invasive surgical stent technology has become popular since the introduction of stents to the medical device market in the United States for vascular and cardiovascular systems, by way of example, in the early 1990s and the introduction of minimally invasive plastic tubular stents for gastrointestinal applications, for instance, since before the early 1980s. For more than a decade, stents have proven to provide an excellent means for implanting into body vessels having a passageway in order to maintain vessel patency and to reinforce, support, repair, create patency by expanding a vessel passageway, or otherwise enhance the performance of the vessel and the vessel passageway. The term "passageway" is understood to be any lumen, chamber, channel, opening, bore, orifice, flow passage, duct, or cavity for the conveyance, regulation, flow, or movement of bodily fluids and/or gases of an animal. As an example, stents have become widely accepted in the medical field for use in the passageways of a heart, blood vessel, artery, vein, capillary, bronchiole, trachea, esophagus, aorta, intestine, bile duct, ureter, urethra, fallopian tube, gastroesophageal, gastroduodenal, gastrointestinal, pylorus, colon, and other locations in a body (collectively, "vessel") to name a few.

In general terms, a stent comprises three parts: a shaft-like tubular body (middle portion of the stent), a proximal end, and a distal end. Stents come in a variety of different configurations. In one example, a stent may further comprise a ring, or stack of rings, each ring being formed of struts and apices connecting the struts, whereby the stent defines an approximately tube-like configuration. Furthermore, the stent surface may not define a truly round cylinder if the struts are straight, because the struts follow a straight line from the apex on one end of the strut to the apex on the other end of the strut. Stents may consist of wire mesh alone (some stents are coated with substances which prevent an inflammatory response) or be cut from a tubular body to form struts and apices, and generally are eventually covered by epithelial tissue after placement within a body.

In addition to their having a variety of configurations, stents also come in different types as defined by the way they expand. For instance, the stents may be non-expanding metallic, polymeric, and plastic stents. In addition, the stents may be expandable. Various types of expandable stents have been described as self-expanding, balloon-expandable, or a combination thereof where the stent is partially self-expanding and partially balloon-expandable.

One particularly useful self-expanding stent is the Z-stent, introduced by Cook Incorporated, due to its ease of manufacturing, high radial force, and self-expanding properties. Examples of the Z-stent are found in U.S. Pat. Nos. 4,580,568; 5,035,706; 5,282,824; 5,507,771; and 5,720,776, the disclosures of which are incorporated in their entirety. The Zilver stent, introduced by Cook Incorporated, is another particularly useful self-expanding stent due to its nitinol platform and use of the Z-stent design properties. Examples of the Zilver stent are found in U.S. Pat. Nos. 6,743,252 and 6,299,635, the disclosures of which are incorporated in their entirety. By way of example only, one or more of these designs have been utilized in stents for applications involving the bronchioles, trachea, thoracic aortic aneurysms (stent-graft), abdominal aortic aneurysms (stent-graft), intestines, biliary tract, and prosthetic venous valve devices. The Z-stent and Zilver stent are capable of being compressed, inserted into a catheter or delivery device, pushed out into the passageway of a vessel, and then self-expanded to help keep the vessel passageway in an open state. A few of the embodiments of devices using one of these stents are the Zilver® 518 biliary self-expanding stent and the Zenith® AAA Endovascular Graft for the endovascular treatment of an abdominal aortic aneurysm.

In yet another embodiment, the self-expanding colonic Z-stent® by Cook provides a self-expanding tubular prosthesis used to maintain patency of malignant colonic strictures in patients having high operative risk or advanced disease. The colonic Z-stent, when fully expanded, typically measures approximately 25 millimeters ("mm") in shaft diameter, approximately 35 mm in diameter at the flared proximal and distal ends, and from about 40 mm to about 120 mm in length from the proximal end to the distal end of the stent. The Zilver® 518 biliary stent, while not a Z-stent, is another example of a self-expanding stent.

A Z-stent and the other types of self-expanding or balloon expandable stents may be compressed to assume a resiliently collapsed tubular configuration having a smaller diameter and may be expanded to assume an expanded tubular configuration having a larger diameter. In its collapsed smaller diameter configuration, the stent may be delivered to the passageway of a vessel and expanded to the larger diameter to help keep the vessel passageway in an open state or otherwise enhance the performance of the vessel.

Delivery System

Stents are usually inserted by endoscopy or other procedures less invasive than a surgical operation, which makes the stents suitable for patients with advanced disease for whom an operation might be too dangerous. The advantages of minimally invasive stent surgery performed with the help of an endoscope are well known and understood in the medical field. As a result, there have been a growing number of devices for use with endoscopes for delivering stents into the observation field and working space of the physician's endoscope, located at the appropriate target site in the field of view, and then deployed.

Stent delivery and placement systems and tools have grown out of the need for implanting these medical devices into endovascular and other body lumens of a patient. In endoscopic and percutaneous delivery systems, a catheter or introducer sheath (collectively, "introducer") constrains the resiliently compressed stent into a collapsed smaller diameter, carries the stent to the target site, and deploys the stent.

With conventional percutaneous (through the skin) stent delivery systems, the physician first positions a hydrophilic wire guide in the vessel passageway, usually under fluoroscopic, radiographic, or endoscopic guidance. Then, the physician inserts a catheter (or other similar percutaneous stent delivery device) over the wire guide and uses the wire guide to maneuver a portion of the delivery system through the vessel passageway and to the desired target site therein.

Depending on the target site and the medical procedure, an endoscope stent placement system may be preferred to a blind stent placement, percutaneous stent placement, or other non-endoscopic stent placement. With a conventional endoscopic stent placement system, the endoscope distal insertion portion carries the stent through any naturally body opening (e.g., the mouth, anus, urethra). The endoscopic stent placement system may comprise a rigid distal insertion portion or a flexible distal insertion portion. The physician moves the rigid distal insertion portion, or flexible distal insertion portion, of the endoscope into position at or near the target site. Then, the physician inserts the stent-carrying introducer through the endoscope working channel and out the distal opening of the working channel and into the physician's observation field and working space.

With larger self-expanding metallic, polymeric, and plastic stents and with larger non-expanding metallic, polymeric, and plastic stents, however, such as stents for colorectal, duodenal, pyloric, or other gastrointestinal or gastroesophageal diseases, to name but a few—the stent or stent delivery introducer may not be placeable through the endoscope working channel or through the endoscope accessory channel. Therefore, improved self-expanding stent delivery systems would be desirable for these larger stents.

As taught herein, the present invention relates to a delivery system that couples externally over the endoscope insert and utilizes the maneuverability and functionality of an endoscope as, so to speak, a "guide wire" to position and deploy the stent. Use of the present invention is not limited to stents, however, and the term "stent" and variants thereof shall describe embodiments according to the invention comprising other self-expanding, balloon expandable, and non-expanding implantable medical devices, such as prosthetic venous valves and other prosthetic articles for placement inside a patient's body.

SUMMARY OF THE INVENTION

Embodiments of the present invention will now be described by way of example, and not by way of limitation, with reference to the accompanying drawings incorporated into this specification, serving to assist those skilled in the art to make and use the invention, and briefly described as follows:

Medical devices for use over endoscopes are provided. In one embodiment, the device for delivering a stent includes an elongate inner member having first and second end portions and a flexible intermediate portion, with openings defining a channel, and further having an inner endoscope insert engaging surface, an outer surface, and a stent abutting restraint disposed at the first end portion. A pusher is disposed at the inner member second end portion in communication with the stent abutting restraint. The device also includes an elongate outer member with distal, proximal, and flexible middle sections, and having openings formed at the proximal and distal sections defining a passageway sized for slideably receiving a portion of the inner member. A chamber is arranged at the outer member distal section and configured to releasably constrain a stent. A puller is disposed at the proximal section and configured to move the outer member relative to the inner member portion outer surface between pre-deployment and deployment positions.

In another embodiment of a medical device for delivering a stent, the medical device has a slideable inner member with a first end portion opening and second portion end opening defining a channel, an inner endoscope slideable engaging surface, an outer surface, and a stent abutting restraint. An elongate pushing member has a distal end in communication with the inner member, and further includes a proximal end, a flexible intermediate section, and a pulling member receiving passageway. An outer member has a distal section and proximal section having openings defining a passageway sized to slideably receive at least a portion of the inner member, a chamber for releasably constraining a stent, slideable between pre-deployment and deployment positions, and having a pulling member link body. Secured to the pulling member link body is a distal connecting end of an elongate pulling member further having a proximal retractor end and a flexible intermediate portion configured to be slideably received in the pushing member passageway.

In a further embodiment, a medical device for delivering a stent has a inner member forming a clip with a distal opening at a first end portion and a proximal opening at a second end portion, the openings defining a channel. The inner member further has an engaging surface and an outer surface, and disposed at the first end portion is a stent abutting restraint. An outer member has a distal section and proximal section having openings defining a passageway sized to slideably receive at least a portion of the inner member, a chamber for releasably constraining a stent, slideable between pre-deployment and deployment positions, and having a pulling member link body. Secured to the pulling member link body is a distal connecting end of an elongate pulling member further having a proximal retractor end and a flexible intermediate portion configured to be slideably received in the pushing member passageway.

Methods of delivering stents are also provided. In one embodiment, a method according to the invention includes providing a stent delivery device comprising an inner member having a first and second end portions defining a channel, an inner endoscope engaging surface, an outer surface, and a stent abutting restraint disposed at the first end portion, and having outer member with proximal and distal sections defining a passageway sized to slideably receive at least a portion of the inner member, the outer member further having a chamber configured to releasably constrain a stent, and having an elongate pulling member with a proximal retractor end, a flexible intermediate portion, and a distal connecting end secured to the outer member. At least a portion of inner member is disposed within the outer member passageway. A pulling member is retracted proximally to move the outer member axially relative to the inner member and between a pre-deployment position and a second deployment position for deploying a stent from the chamber.

BRIEF DESCRIPTION OF THE DRAWINGS

Embodiments of the present invention will now be described by way of example only, and not by way of limitation, with reference to the accompanying drawings briefly described as follows:

FIGS. 1C and 1D show longitudinally sectioned side views of an alternative embodiment of a latching member.

FIGS. 18A, 18B, and 18C are perspective partial views of alternative embodiments of an outer member according to the invention.

DETAILED DESCRIPTION OF THE PREFERRED EMBODIMENTS

Although not limited in its scope or applicability, the present invention relates generally to a device used with endoscopes, and methods of using those devices. More particularly, and by way of illustration and not by way of limitation, the present invention relates to an over the endoscope introducer for devices such as stents. The description below depicts a self-expanding stent, but it will be appreciated that the invention may also be utilized with non-expanding metallic, polymeric, and plastic stents, balloon-expandable stents, or a combination thereof where the stent is partially self-expanding, partially non-expanding and partially balloon-expandable. The description of a self-expanding stent, therefore, should not be limiting.

For the purpose of promoting an understanding of the principles of the invention, the following provides a detailed description of embodiments of the invention as illustrated by the drawings as well as the language used herein to describe various aspects of the invention. The description is not intended to limit the invention in any manner, but rather serves to enable those skilled in the art to make and use the invention. As used herein, the terms comprise(s), include(s), having, has, with, contain(s) and variants thereof are intended to be open ended transitional phrases, terms, or words that do not preclude the possibility of additional steps or structure.

Figure 1:
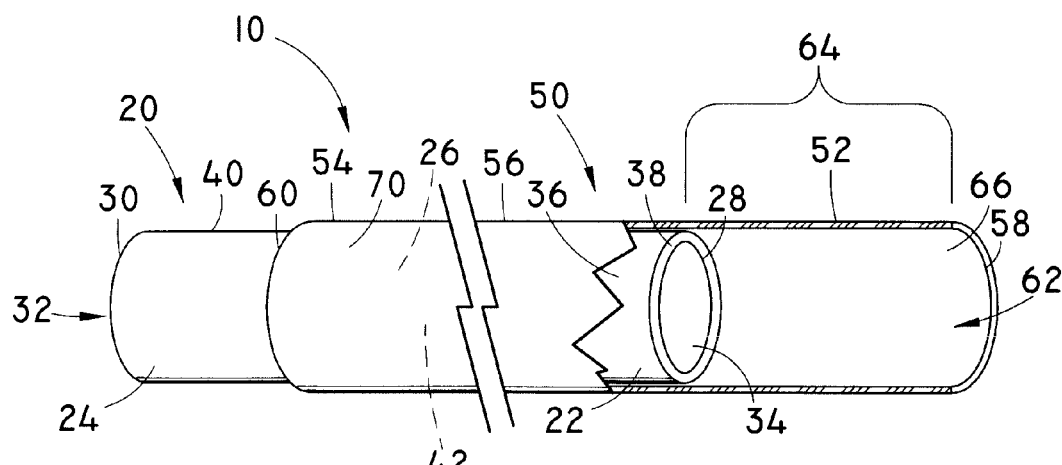
FIG. 1 provides a perspective partial view, broken away, of a medical device according to one embodiment of the invention having an elongate inner member and an elongate outer member.

FIG. 1 shows over-the-scope stent introducer 10 according to one embodiment of the invention for delivering a stent (e.g., a non-expanding stent, a self-expanding stent, a balloon-expandable stent, or a combination thereof, individually and collectively referred to as a "stent" except where otherwise noted). This embodiment comprises an elongate tubular inner member 20 and an elongate tubular outer member 50. In describing embodiments of the invention, an inner member 20 could be any shaft-like, rounded, oblong, circular, rectangular, square, tube-like, tubular, cylindrical, or generally rod-like structure for detachably engaging at least a portion of an insertion section of an endoscope. Inner and outer members 20, 50, respectively, typically comprise polytetrafluoroethylene such as TEFLON by E.I. du Pont de Nemours and Company or other fluorine-containing resins, polyether block amides or other thermoplastics, any suitable flexible polymer tube, reinforced metal tubing, work hardened surgical stainless steel, or any conventional material not subject to excessive stretching or compression during axial pulling or pushing while capable of being flexible with the endoscope during use. Furthermore, the construction of the inner member 20 or outer member 50 may comprise a coiled sheath, reinforced metal, or a polymer exhibiting sufficient flexibility where desired and capable of transferring tensile and/or compressive forces.

The term "elongate," in describing any of the embodiments, means long. Because the overall length of the endoscope may vary as discussed above, so too may the embodiments of the inner and outer members 20, 50, respectively, vary from a length of between about 630 millimeters ("mm") and about 2800 mm, or may be shorter or longer as desired. The diameter of the members 20, 50, respectively, may vary as well from one embodiment to the next, depending on the type of endoscope for which the physician intends to use the over-the-scope stent introducer 10. Because the inner member 20 fits over at least a portion of an endoscope insert, the inner member inner diameter may comprise an endoscope engaging diameter of at least about 5.0 mm up to about 19.0 mm, or may be greater or less than this range at certain positions along the length of the inner member 20 given any tapering in the endoscope insert outer diameter. The outer member 50 inner diameter would be at least as great as the inner member outer diameter to accommodate slideably receiving at least a portion of the inner member 20, or from approximately 5.0 mm to approximately 19.0 mm, or may be greater or less than this range at certain positions along the length of the outer member 50 given the tapering in the outer diameter of the inner member 20 or the endoscope insert.

The inner member 20 has a distal first end portion 22, a proximal second end portion 24, and a flexible intermediate portion 26. The flexibility may vary along the length of the intermediate portion 26, and may be flexible at certain portions while being more or less rigid at other portions. Furthermore, the distal first end portion 22 may also be flexible. The first end portion 22 and intermediate portion 26 are configured to bend with the portion of the flexible endoscope insert.

The first end portion 22 and second end portion 24 include openings 28, 30, respectively, defining a channel 32 therebetween. The channel may be any passageway, lumen, channel, bore, flow passage, duct, or cavity configured for slidably receive an endoscope insert and comprising an inner endoscope insert engaging surface 34. Also, the inner member 20 includes an outer surface 36 disposed circumferentially about the inner member. The inner member 20 has a stent abutting restraint 38 disposed at the distal first end portion. The stent abutting restraint 38 as used to describe any embodiments of the invention should not be construed to include the stent 12 (not shown), but is a restraint configured for limiting the proximal movement of a non-expanding, a self-expanding, and/or a balloon expandable (or combination thereof) stent 12 relative to the outer member 50 during deployment.

The endoscope engaging surface 34 should not be construed to include the endoscope, but is only used to describe an inner surface of the inner member 20 configured to detachably engage an endoscope insert. The engaging surface 34 may be a slideably engageable surface for allowing the inner member to be substantially freely slideable (save for some natural friction between abutting surfaces of the engaging surface 34 and the endoscope) relative to the endoscope insert 11' in use during deployment of a stent. Alternatively, when the physician desires that the inner member be less freely slideable relative to the endoscope insert 11' after the inner member fits over at least a portion of an endoscope insert 11', then the inner endoscope engaging surface 34 may be a coupling engageable surface configured to detachably couple the inner member and endoscope insert after the inner member has been slid over a portion of an endoscope insert. In one embodiment, the coupling engageable surface is a friction fit between the inner endoscope engage surface 34 and the endoscope insert. Thus, the inner member endoscope insert engaging surface 34 may be a slideably engageable surface configured to dispose substantially concentrically over a majority of an endoscope insert 11' or configured to dispose substantially concentrically over a majority of an endoscope insert 11' and comprise a friction fit engagement sufficient to detachably operatively the inner member inner surface endoscope engaging surface 34 and the endoscope insert 11'.

The inner member 20 further includes a pusher 40 positioned at the proximal second end portion 24 in communication with the first end portion stent abutting restraint 38. The term "communication" in describing any embodiments means any two features directly or indirectly—there may be other intermediate features, such as (by way of example only) the flexible intermediate portion 26—associated and capable of transferring tensile and/or compressive forces from the first feature to the second feature. The inner member pusher 40 has sufficient stiffness to urge the inner member distal first end portion 22 distally and to keep a stent abutting restraint 38 from prolapse as a result of the outer member inner chamber 64 being pulled proximally over the inner member distal first end portion 22. By way of illustration and not by way of limitation, the pusher 40 may be a handle that gives the physician control over the axial movement of the inner member 20 during stent deployment. For example, the handle may be a prehensile attachment, a gripping surface, a grooved contour, or handle assembly having a pivotal handle member or actuation device.

FIG. 1 also shows that the over-the-scope stent introducer 10 comprises an elongate tubular outer member 50 having a distal section 52, a proximal section 54, and a flexible middle section 56. The flexibility may vary along the length of the middle section 56, and may be flexible at portions while being more or less rigid at other portions. Furthermore, the distal section 52 may also be flexible. The distal section 52 and middle section 56 are configured to bend with the portion of the flexible endoscope insert.

The distal section 52 and proximal section 54 include openings 58, 60, respectively, defining a passageway 62. The passageway may be any passageway, lumen, channel, bore, flow passage, duct, or cavity sized for slideably receiving a portion 42 of the inner member 20.

Also, the outer member 50 includes an inner chamber 64 (or stent carrying inner chamber 64) disposed in the passageway 62 of the outer member distal section 52. The inner chamber 64 may be configured to be any volume along a portion of the length of the passageway 62 within the distal section 52 sufficient to releasably constrain a stent. The inner chamber 64 may releasably constrain a radially compressed self-expanding, a balloon expandable stent, or a non-expanding stent such as a plastic tube that stays in the patient at a target site because the outer diameter is sufficiently larger than the vessel passageway such as to stretch the vessel and thereby stay in place due to the vessel's elastic radially compressive forces. Moreover, the chamber 64, inner chamber 64, or term "stent carrying inner chamber" as used to describe any embodiments of the invention should not be construed to include the stent, but is used to describe a cavity within the distal section comprising a restraint such as an outer member inner surface 66 configured for releasably constraining a radially compressed self-expanding stent. In one embodiment of the invention, the over-the-scope stent introducer 10 further comprises a radially compressed self-expanding stent, a balloon expandable stent, or a non-expanding stent in the inner chamber 64.

Also, the outer member 50 includes a puller 70 disposed at the outer member proximal section 54. By way of illustration and not by way of limitation, the puller 70 may be a handle, described above in context of the pusher 40, in communication with the distal section 52 and configured to move the outer member distal section inner chamber 64 between a pre-deployment position 72 (see FIG. 2) and a deployment position 74, 76 (see FIGS. 4A, 4B).

FIGS. 1A, 1B, 1C, 1D, 1E, 1F, 1G, and 1H show embodiments of optional latching members 230, 240, 250, 260 configured for detachably operatively coupling the outer member proximal section 54, 154 (FIGS. 1, 1A, 1C, 1E, 1H, 11, 15A, 15B, 16) and the inner member proximal second end portion 24, 124 (FIGS. 1, 1E, 1G, 1H, 11, 16) and/or the inner member outer surface 36, 136 (FIGS. 1, 1A, 1C, 1E, 1H, 3B, 6B, 6C, 9, 11, 12, 13B, 14, 16, 17A-17C, 19B-19D). Likewise, the latching members 230, 240, 250, 260 are configured for detachably operatively coupling the inner member second end portion 24, 124 and an endoscope insert proximal section 111 (FIGS. 5, 6A-6B, 7-8, 10A-10B).

Figure 1A:
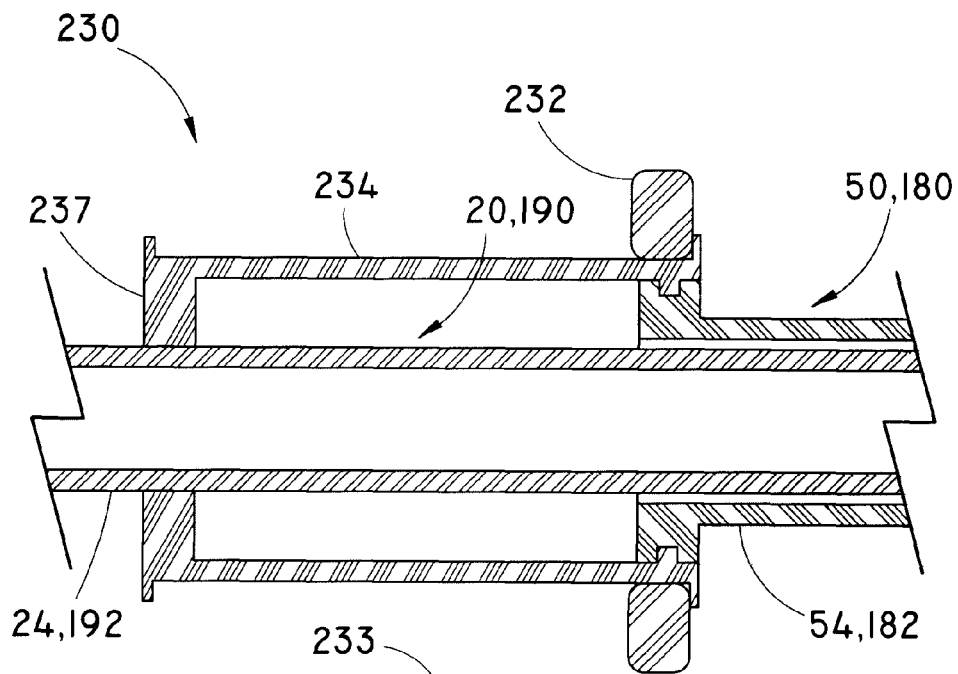
FIGS. 1A and 1B show longitudinally sectioned side views of an embodiment of a latching member configured for detachably operatively coupling the outer member proximal section and the inner member proximal second end portion and/or the inner member second end portion and an endoscope insert proximal section.
Figure 1B:
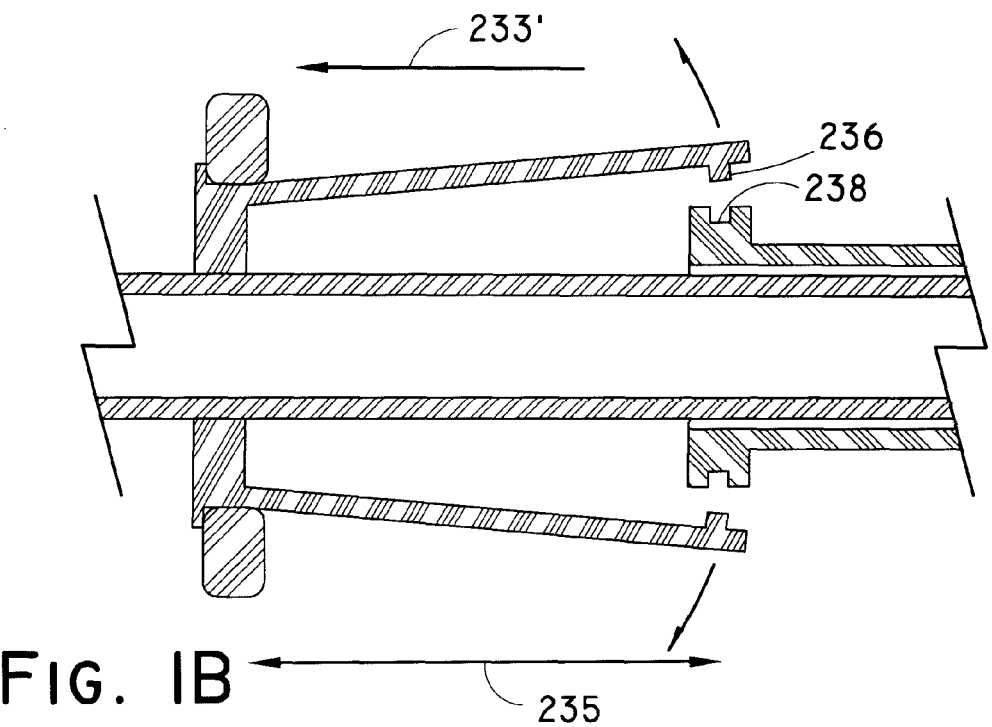

In FIG. 1A, the latching member 230 comprises a sliding keeper 232 and a spring arm 234. FIG. 1B shows the spring arm 234 comprising a connecting member 236 that operatively couples to a socket 238. The sliding keeper 232 engages the connecting member 236 to the socket 238 in a latching position 233 (FIG. 1A), and when moved to an unlatching position 233' (FIG. 1B), the sliding keeper 232 disengages the connecting member 236 from the socket 238. In this embodiment, the spring arm 234 is radially biased so that movement of the sliding keeper 232 to the unlatching position 233' results in the spring arm 234 moving the connecting member 236 radially away from the socket 238.

By way of example only and not by way of limitation, the terms "operatively coupling," "operatively coupled," "coupling," "coupled," and variants thereof are not used lexicographically but instead are used to describe embodiments of the invention having a point, position, region, section, area, volume, or configuration at which two or more things are mechanically, chemically, and/or chemical-mechanically bonded, joined, adjoined, connected, associated, united, mated, interlocked, conjoined, fastened, held together, clamped, crimped, friction fit, pinched, press fit tight, nested, wedged, and/or otherwise associated by a joint, a junction, a juncture, a seam, a union, a socket, a melt bond, glue, adhesives, resins, welding (laser, spot, etc.), soldering, brazing, adhesives, chemical bonding materials, implanted arrangement, or combinations thereof. Embodiments of latching members include latches, screws, clamps, cams, hooks, sleeves, collets, and the like.

The secured end 237 of spring arm 234 is fastened to or integral with the inner member proximal second end portion 24 such that the proximal section 54 of the outer member 50 is operatively coupled at or near the second end portion 24 of the inner member 20. The latching member 230 may operatively couple the second end portion 24 and proximal section 54 at a predetermined position relative to each other, which position may be set by the length of the spring arm 234 or the position of the latching member 230 along the length of the inner member. In the latching position 233, the stent at the outer member stent carrying chamber 64 is not allowed to prematurely deploy, because the outer member 50 is not allowed to move relative to the inner member 20 when the sliding keeper 232 engages the connecting member 236 to the socket 238 in a latching position 233 (FIG. 1A).

When the sliding keeper 232 is moved to an unlatching position 233', however, then the outer member is allowed to move proximally the distance 235, which should be at least the length of the stent so that the stent is fully deployed from the outer member chamber. While the latching member 230 is shown fastened to or integral with the inner member proximal second end portion 24, there may be a second latching member 230 (or alternatively in lieu of the first latching member 230) comprising a secured end 237 that is clamp or fastened to the insert proximal section 111 such that the proximal second end portion 24 of the inner member 20 is operatively coupled at or near the insert proximal section 111 of the endoscope insert 11'.

In an alternative embodiment of the invention described below relating to FIGS. 11 through 19, the secured end 237 of spring arm 234 is fastened to or integral with a proximal retractor end 192 of a pulling member 190. Accordingly, a proximal end 182 of an elongate pushing member 180 is detachably operatively coupled at or near the proximal retractor end 192 of the pulling member 190.

In FIG. 1C, the latching member 240 comprises a sliding keeper 242 comprising a spring actuated spring arm 244. FIG. 1C shows the spring actuated spring arm 244 comprising a spring 244' and a connecting member 246, wherein the connecting member 246 is configured to operatively couple to a socket 248 formed in the proximal section 54 of the outer member 50. The spring actuated spring arm 244 and connecting member 246 may be movably housed in an optional housing 242' formed in the proximal section 54 of the outer member 50. The optional housing 242' is configured such that the sliding keeper 242 may slide over the optional housing 242'. Optionally, the connecting member 246 comprises a retainer 249 is configured to slideably fit within the socket 248 while also being configured to hold the connecting member 246 to the outer member 50 so that the connecting member 246 does not separate from the outer member 50 as a result of the spring actuated spring arm 244.

The sliding keeper 242 holds down the connecting member 246 in an engaging position into the socket 248 in a latching position 243 (FIG. 1C), and when the sliding keeper 242 is moved to an unlatching position 243' (FIG. 1D), the spring actuated spring arm 244 is radially biased by the spring 244' to move radially 247 and thereby disengages the connecting member 246 from the socket 248 to the unlatching position 243'. Optionally, the sliding keeper 242 further comprises a bevel 241 such as an inclined connecting member inner face on the distal portion of the sliding keeper 242. The bevel 241 is thereby configured to facilitate a one-handed procedure whereby the sliding keeper 242 slides distally, for example, the over an optional head 246' of the connecting member 246 so as to cause the connecting member 246 to move radially inwardly toward the socket 248.

The latching member 240 may operatively couple the second end portion 24 and proximal section 54 at a predetermined position relative to each other, which position may be set by the as set by the position of the socket 248 along the length of the outer member. In one embodiment, there are many sockets 248 along the length of the proximal section 54 of the outer member 50 such that in order to give the physician many different locking positions in order to accommodate stents of many lengths. In a latching position 243, the stent at the outer member stent carrying chamber 64 is not allowed to prematurely deploy, because the outer member 50 is not allowed to move relative to the inner member 20 when the sliding keeper 242 engages the connecting member 246 to the socket 248 in a latching position 243 (FIG. 1C). When the sliding keeper 242 is moved to an unlatching position 243', however, then the outer member is allowed to move proximally the distance 245, which should be at least the length of the stent so that the stent is fully deployed from the outer member chamber.

In an alternative embodiment, there may be a second latching member 240 (or alternatively in lieu of the first latching member 240) comprising a spring actuated spring arm 244 having a spring 244' and a connecting member 246 are on the proximal second end portion 24 of the inner member 20, and the socket 248 formed in the insert proximal section 111. The sliding keeper 242 is moved to a latching position 243 such that the proximal second end portion 24 of the inner member 20 is operatively coupled at or near the insert proximal section 111 of the endoscope insert 11'.

In an alternative embodiment of the invention described below relating to FIGS. 11 through 19, the latching member 240 may detachably operatively couple a proximal retractor end 192 of a pulling member 190 and a proximal end 182 of an elongate pushing member 180 is operatively coupled at or near the proximal retractor end 192 of the pulling member 190. In one embodiment, the spring actuated spring arm 244 (and optionally the housing 242') is formed at the proximal end 182 of the elongate pushing member 180, the socket 248 optionally may be formed in the proximal retractor end 192 of the pulling member 190, and the sliding keeper 242 works as described above.

Figure 1E:
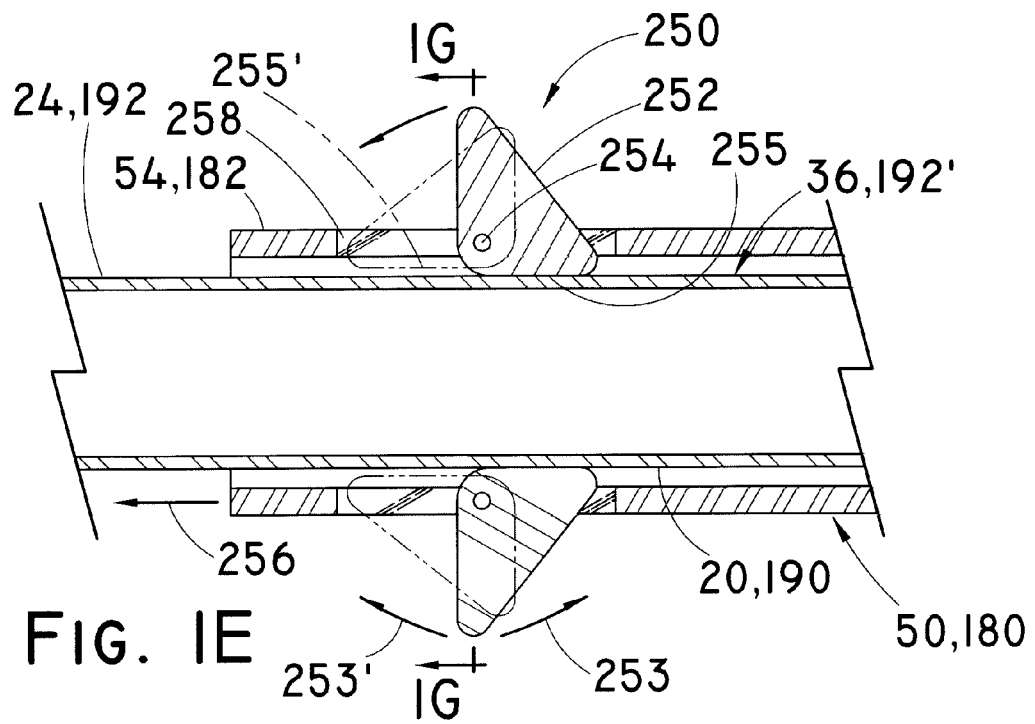
FIG. 1E shows a longitudinally sectioned side views of another embodiment of a latching member.
Figure 1F:
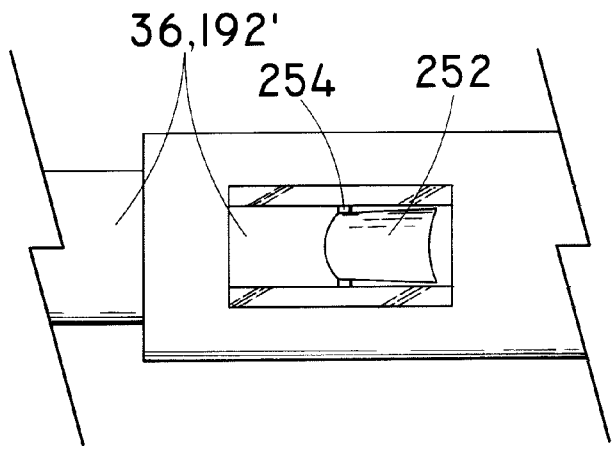
FIG. 1F shows a perspective top view of the latching member according to FIG. 1E.
Figure 1G:
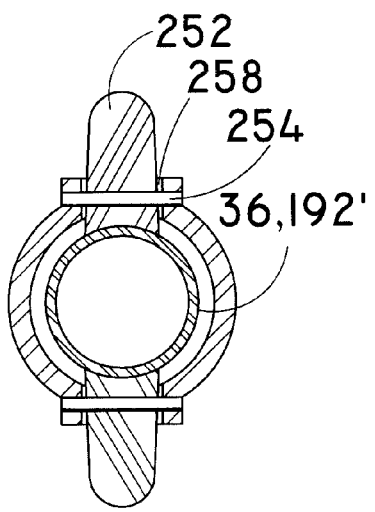
FIG. 1G is a cross sectional view of FIG. 1E taken along the lines 1G-1G.

FIGS. 1E, 1F, and 1G show an alternative embodiment of a latching member 250 comprising a cam lock 252 and a rotation arm 254. FIGS. 1E, 1F, and 1G show the cam lock 252 disposed within a socket 258 formed at the proximal section 54 of the outer member and rotatable about the rotation arm 254 such that the cam lock 252 operatively couples to the outer surface 36 of the inner member 20 at or near proximal second end portion 24. The cam lock 252 has a braking surface 255 that engages the inner member outer surface 36 in a latching position 253 (FIG. 1A), and when moved to an unlatching position 253' (FIG. 1B), has a sliding surface 255' that is slideable and/or offset from the inner member outer surface 36 so as to disengage cam lock 252 from the inner member 20. In an alternative embodiment, the cam lock 252 has a braking surface 255 that does not engage the inner member outer surface 36 but instead interlocks within a socket of the inner member.

In the latching position 253, the stent at the outer member stent carrying chamber 64 is not allowed to prematurely deploy, because the outer member 50 is not allowed to move relative to the inner member 20 when the braking surface 255 of the cam lock 252 engages the inner member outer surface 36 (FIGS. 1E, 1F). When the cam lock 252 is rotated about the rotation arm 254 to an unlatching position 253', however, then the outer member is allowed to move proximally the distance 256, which should be at least the length of the stent so that the stent is fully deployed from the outer member chamber. While the latching member 250 is shown fastened to or integral with the outer member proximal section 54, there may be a second latching member 250 (or alternatively in lieu of the first latching member 250) placed on the inner member proximal second end portion 24 such that the proximal second end portion 24 of the inner member 20 is operatively coupled at or near the insert proximal section 111 of the endoscope insert 11'.

The latching member 250 gives the physician a continuum of positions of where to lock the outer member into position relative to the inner member. Thus, if the physician preloads a short stent, then the physician may want the proximal end of outer member locked into place closer to the proximal end of the inner member. If the physician preloads a long stent then he may want the proximal end of outer member locked into place more distally of the proximal end of the inner member.

In another alternative embodiment of the invention described below relating to FIGS. 11 through 19, the latching member 250 may be fastened to or integral with a proximal end 182 of an elongate pushing member 180 such that the proximal end 182 of the elongate pushing member 180 is operatively coupled at or near a proximal retractor end 192 of a pulling member 190. The cam lock 252 disposed within a socket 258 formed at the proximal end 182 of the elongate pushing member 180 and rotatable about the rotation arm 254 such that the cam lock 252 operatively couples to an outer surface 192' of the proximal retractor end 192 of the pulling member 190. The cam lock 252 has a braking surface 255 that engages the outer surface 192' in a latching position 253 (FIG. 1A), and when moved to an unlatching position 253' (FIG. 1B), has a sliding surface 255' that is slideable and/or offset from the outer surface 192' so as to disengage cam lock 252 from the pulling member 190.

Figure 1H:
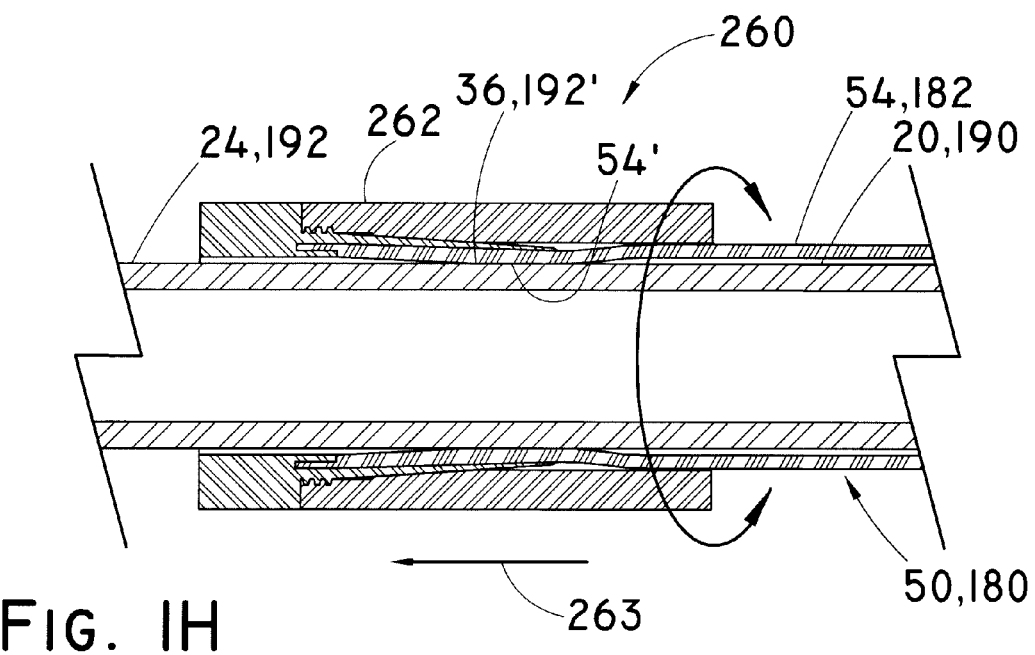
FIGS. 1H and 1I show longitudinally sectioned side views of another embodiment of a latching member.
Figure 1I:
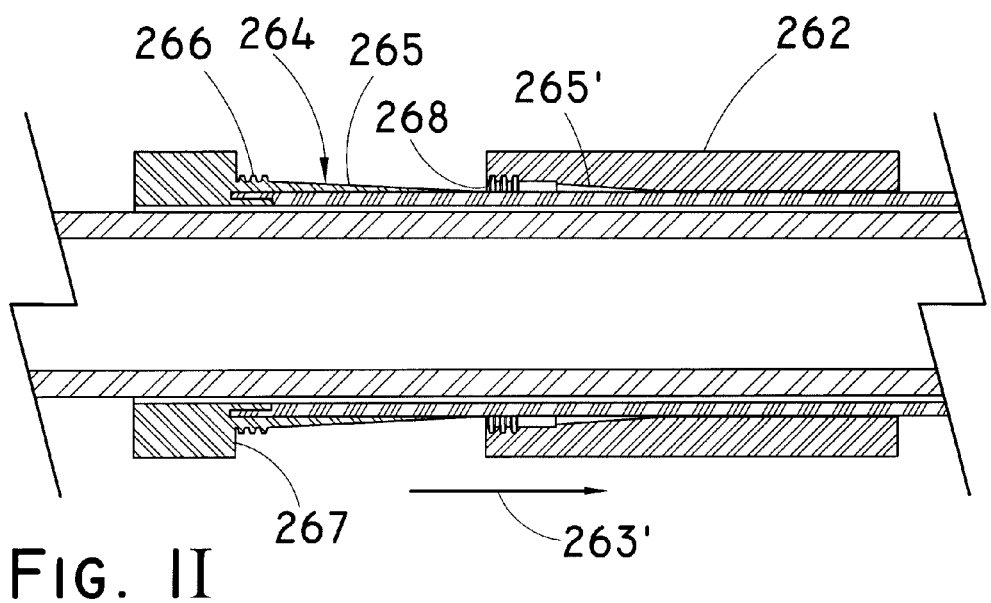

FIGS. 1H and 1I show yet another embodiment of a latching member 260 comprising a collar 262 that advances over a collet 264 that compresses against the inner member outer surface 36 in order to hold the outer member 50 stationary relative to the inner member 20 and prevent premature deployment. The collet 264 has an inclined side 265' and an inclined surface 265. During advancement of the collar 262 over the collet 264, the inclined side 165' and the inclined surface 265 are positioned within the collar 262, and the inclined surface 265 compresses the outer member inner surface 54' against the inner member outer surface 36. In one embodiment, the collar 262 may compress the collet inclined surface 265 against the inner member outer surface 36. In another embodiment, the collar 262 has a connecting member 268 comprising inner threads and a socket 266 comprising outer threads that are engaged by rotatating the collar 262 so as to operatively couple the collar to the connecting member 268 in a latching position 263 (FIG. 1H) up against the proximal stop 267 (see FIG. 1I) that stops further proximal movement of the collar. When the collar 262 is moved to an unlatching position 263' (FIG. 1I), the collar 262 disengages the socket 268 from the connecting member 266.

The latching member 260 gives the physician a continuum of positions of where to lock the outer member into position relative to the inner member. Thus, if the physician preloads a short stent, then the physician may want the proximal end of outer member locked into place closer to the proximal end of the inner member. If the physician preloads a long stent then he may want the proximal end of outer member locked into place more distally of the proximal end of the inner member.

While the latching member 260 is showed fastened to or integral with the outer member proximal section 54, there may be a second latching member 260 (or alternatively in lieu of the first latching member 260) at or near the proximal second end portion 24 of the inner member 20 such that the proximal second end portion 24 of the inner member 20 is operatively coupled at or near the insert proximal section 111 of the endoscope insert 11'. In another alternative embodiment of the invention described below relating to FIGS. 11 through 19, the latching member 250 may be fastened to or integral with a proximal end 182 of an elongate pushing member 180 such that the proximal end 182 of the elongate pushing member 180 is operatively coupled at or near a proximal retractor end 192 of a pulling member 190. The latching member 260 comprising a collar 262 that advances over a collet 264 that compresses against an outer surface 192' of the proximal retractor end 192 of the pulling member 190 in order to hold the elongate pushing member 180 stationary relative to the pulling member 20 and prevent premature deployment.

Alternative embodiments of latching members 230, 240, 250, and 260 may comprise latches, screws, clamps, cams, hooks, sleeves, collets, and the like.

Figure 2:
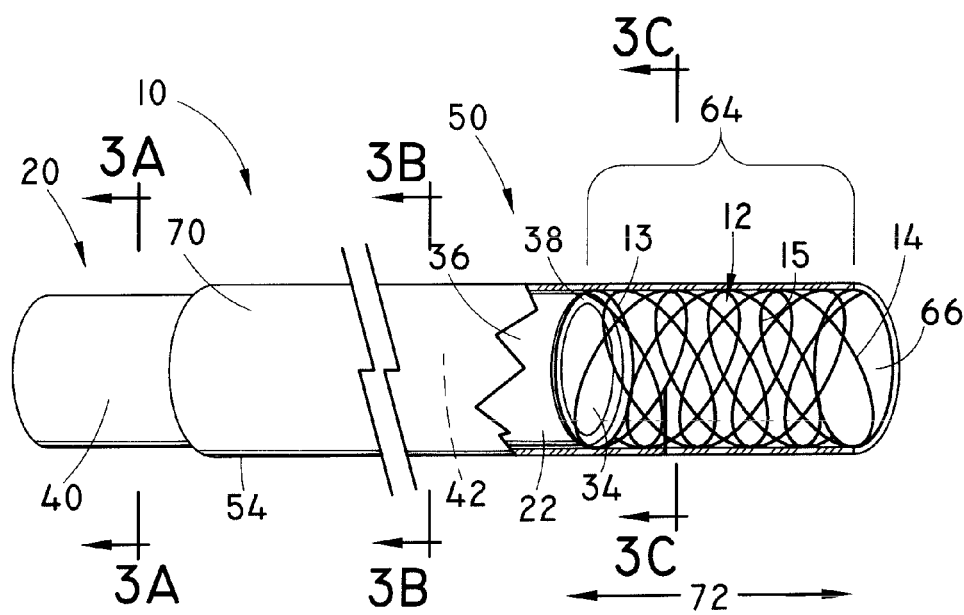
FIG. 2 provides a perspective partial view, broken away, of a medical device according to an embodiment of the invention having an elongate inner member, an elongate outer member, and a self-expanding stent in a radially compressed state in a schematically illustrative pre-deployment position.

FIG. 2 shows that the outer member 50 is axially slideable relative to the inner member portion outer surface 36. FIG. 2 further shows an over-the-scope stent introducer 10 for delivering a stent comprising an elongate tubular outer member 50 being substantially concentric to and slideable over an elongate tubular inner member 20 as previously described in connection with FIG. 1. Otherwise stated, the elongate tubular inner member is received within the passageway of the elongate tubular outer member. Indeed, the physician may push on the inner member pusher 40 in order to hold the inner member substantially stationary while the physician pulls on the outer member puller 70 at or near the outer member proximal section 54 so as to slide the outer member over the inner member outer surface 36.

As schematically depicted in FIG. 2, a stent 12 has proximal and distal ends 13, 14, respectively, and an intermediate portion 15. The stent 12 may be a radially compressed self-expanding stent, a balloon expandable stent, or a non-expanding stent that is releasably contained within the outer member chamber 64. An inner member restraint 38 abuts the stent proximal end 13. Once a stent 12 (e.g., a self-expanding stent in a radially compressed state, a balloon expandable stent, or a non-expanding stent) is loaded by any conventional means in the outer member chamber 64 of the over-the-scope stent introducer 10, the inner member stent abutting restraint 38 is positioned at the distal first end portion 22 and configured to control proximal axial movement of a stent 12 relative to that of the inner member 20. In one embodiment, the restraint 38 is sized to be large enough to make sufficient contact with the loaded proximal end 13 of the stent 12. For example, the restraint 38 may be the circumferential wall thickness of the inner member first end portion 22 (e.g., distal end face of the inner member first end portion 22) for abutting against the stent proximal end 13, or the restraint 38 may be any protuberance, protrusion, bulge, bow, convex, bump, knob, raising, lump, or combination thereof for abutting against the stent proximal end 13. In addition to helping to stop the stent's proximal movement in a non-deployed state, the restraint 38 helps to "push" a stent 12 out of the chamber 64 by preventing the stent from migrating proximally when the outer member 50 retracts proximally relative to the inner member 20 to deploy the stent 12. Optionally, the restraint 38 may be radiopaque so as to aid in positioning stent 12 within the target site.

As should be understood, no figure or feature is intended to be to scale, nor is one feature relative to another feature to scale. Rather, the figures and their features are intended to convey the various types of embodiments, and features of embodiments, according to the invention.

Figure 3A:
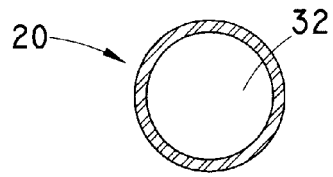
FIG. 3A is a cross sectional view of FIG. 2 taken along the lines 3A-3A.

FIG. 3A shows a cross sectional view of FIG. 2 taken along the lines 3A-3A. This Figure includes the inner member 20 and its channel 32 configured to slideably receive an endoscope insert 11'. Optionally, the inner member channel 32 may detachably mount to an endoscope 11 and/or the endoscope insert proximal section 111 such as, by way of example only and not by way of limitation, one of the embodiments of optional latching members 230, 240, 250, 260 shown in FIGS. 1A, 1B, 1C, 1D, 1E, 1F, 1G, and 1H or latches, screws, clamps, cams, hooks, sleeves, collets, and the like, which for clarity of figures are not shown in FIGS. 3A, 3B, and 3C.

Figure 3B:
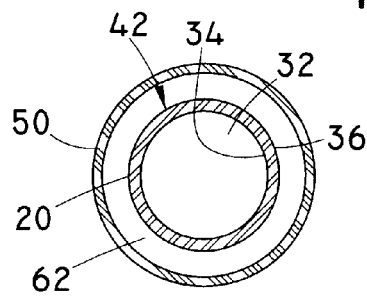
FIG. 3B is a cross sectional view of FIG. 2 taken along the lines 3B-3B.

FIG. 3B shows a cross sectional view of FIG. 2 taken along the lines 3B-3B. This Figure includes a portion 42 of the inner member 20 having an inner member channel 32, inner endoscope insert engaging surface 34, and an outer surface 36. The inner member portion 42 is shown inserted into the passageway 62 of the outer member 50, wherein the outer member 50 is substantially concentric to the inner member 20 and axially slideable over the inner member portion outer surface 36.

Figure 3C:
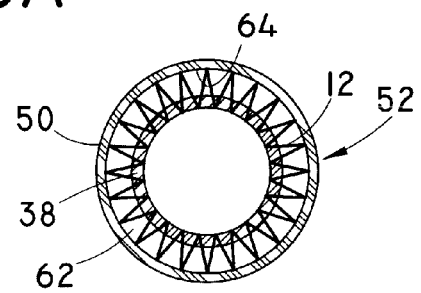
FIG. 3C is a cross sectional view of FIG. 2 taken along the lines 3C-3C.

FIG. 3C shows a cross sectional view of FIG. 2 taken along the lines 3C-3C. The Figure includes an end-on view to show the inner member restraint 38, an outer member 50, and the stent 12 releasably contained within the outer member chamber 64. The inner chamber 64 is disposed in the passageway 62 of the outer member distal section 52 and configured to releasably contain a stent 12.

Figure 4A:
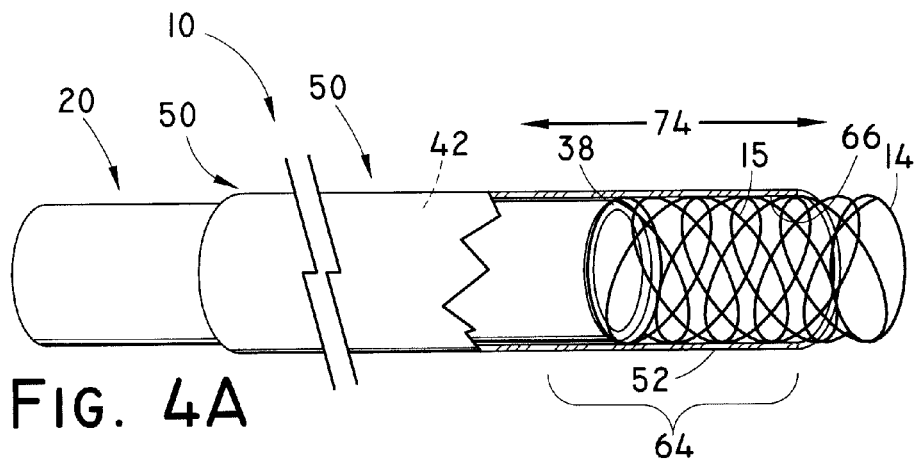
FIG. 4A provides a perspective partial view, broken away, of a medical device according to one embodiment of the invention having an elongate inner member, an elongate outer member, and a self-expanding stent in a radially compressed state in a schematically illustrative second deployment position.

FIG. 4A shows FIG. 2 having a distal section inner chamber 64 positioned at a deployment position 74. Shown is a self-expanding stent distal end 14 partially deploying into a volume exterior to the outer member distal section 52, but the deployment position 74 also would partially deploy a balloon expandable stent and a non-expanding stent into a volume exterior to the outer member distal section 52.

Figure 4B:
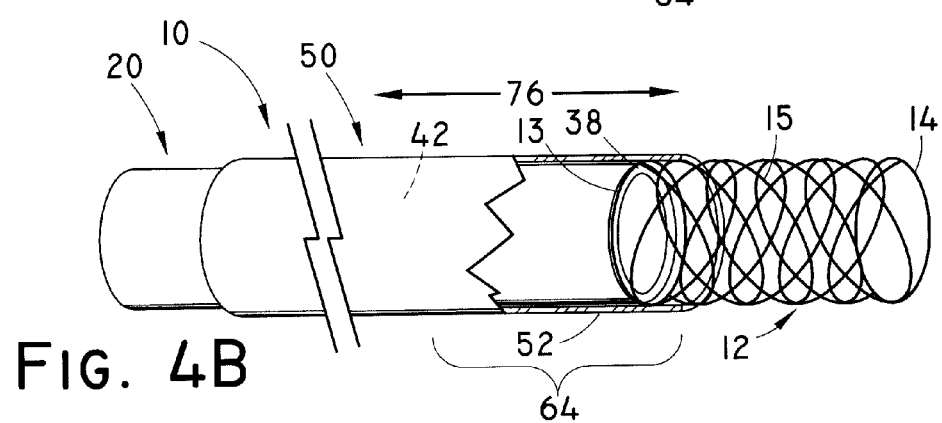
FIG. 4B is a perspective view of FIG. 4A in another second deployment position.

FIG. 4B shows FIG. 4A having a distal section inner chamber 64 positioned at a second deployment position 76. The self-expanding stent distal end 14 and intermediate portion 15 have deployed into a volume exterior to the outer member distal section 52. A third deployment position (not shown) would deploy the stent distal end 14, intermediate portion 15, and proximal end 13 to fully deploy the stent 12 into a volume exterior to the outer member distal section 52 and at a target site within the patient's body.

Figure 5:
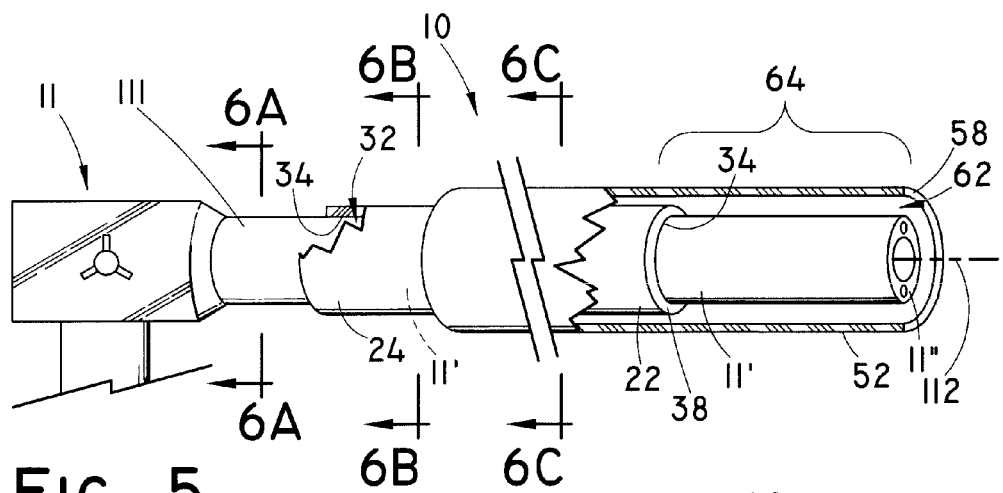
FIG. 5 provides a perspective partial view, broken away, of a medical device according to one embodiment of the invention detachably engaging at least a portion of an endoscope insert.

FIG. 5 shows an embodiment of the over-the-scope stent introducer 10 of FIG. 1 detachably mounted to an endoscope 11. The endoscope comprises an elongate endoscope insert 11' having an insert distal end 11" and an insert proximal section 111, the insert distal end 11" comprises a longitudinal axis 112. As used herein and throughout to describe embodiments of the invention, the term "longitudinal axis" should be considered to be an approximate lengthwise axis, which may be straight or may at times even be curved in an embodiment of the endoscope insert 11' that is flexible or partially flexible.

The insert 11' has been inserted into the inner member channel 32 and the inner endoscope engaging surface 34 detachably engages a portion of the insert 11'. The insert distal end 11" is shown extending distally beyond the inner member first end portion 22 and at or near the outer member distal section opening 58. Optionally, the over-the-scope stent introducer 10 could be detachably mounted to an endoscope 11 such that the insert distal end 11" is proximal to the inner member restraint 38. Alternatively, the over-the-scope stent introducer 10 could be detachably mounted to an endoscope 11 such that the insert distal end 11" extends distally beyond the outer member distal section opening 58, which may allow the insert distal end 11" to be positioned at the target site before the outer member distal section 52 is slid distally into place.

The inner member endoscope insert engaging surface 34 may be a slideably engageable surface configured to dispose substantially concentrically over a majority of an endoscope insert 11' or configured to dispose substantially concentrically over a majority of an endoscope insert 11' and comprise a friction fit engagement sufficient to detachably operatively the inner member inner surface endoscope engaging surface 34 and the endoscope insert 11'. In an alternative embodiment, optional latching members 230, 240, 250, 260 shown in FIGS. 1A, 1B, 1C, 1D, 1E, 1F, 1G, and 1H or latches, screws, clamps, cams, hooks, sleeves, collets, and the like may operatively couple the insert proximal section 111 and the inner member proximal second end portion 24.

Figure 6A:
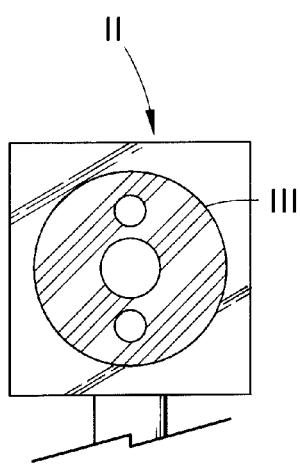
FIG. 6A is a cross sectional view of FIG. 5 taken along the lines 6A-6A.

FIG. 6A shows a cross sectional view of FIG. 5 taken along the lines 6A-6A. This Figure schematically depicts the insert proximal section 111 of the endoscope 11.

Figure 6B:
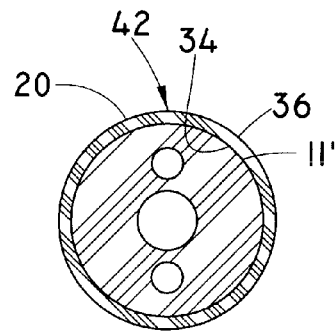
FIG. 6B is a cross sectional view of FIG. 5 taken along the lines 6B-6B.

FIG. 6B shows a cross sectional view of FIG. 5 taken along the lines 6B-6B. This FIG. 6B includes an insert 11' inserted inside the inner member channel 32 (shown in FIG. 3B) of a portion 42 of the inner member 20, inner endoscope engaging surface 34, and an outer surface 36. The endoscope 11 is not shown. The portion 42 is configured to dispose substantially concentrically over a majority of the endoscope insert 11'.

Figure 6C:
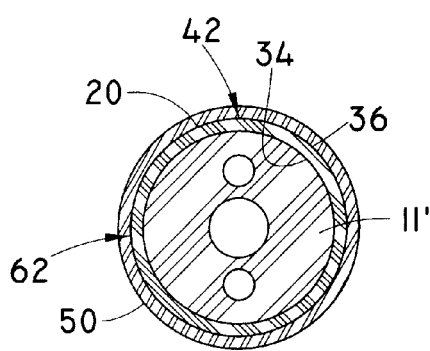
FIG. 6C is a cross sectional view of FIG. 5 taken along the lines 6C-6C.

FIG. 6C shows a cross sectional view of FIG. 5 taken along the lines 6C-6C. This FIG. 6C includes an insert 11' being received in the inner member channel 32 (shown in FIG. 3B) of a portion 42 of the inner member 20 having an inner endoscope engaging surface 34 and an outer surface 36. The inner member portion 42 is shown inserted into the passageway 62 of the outer member 50. The endoscope 11 is not shown.

Figure 7:
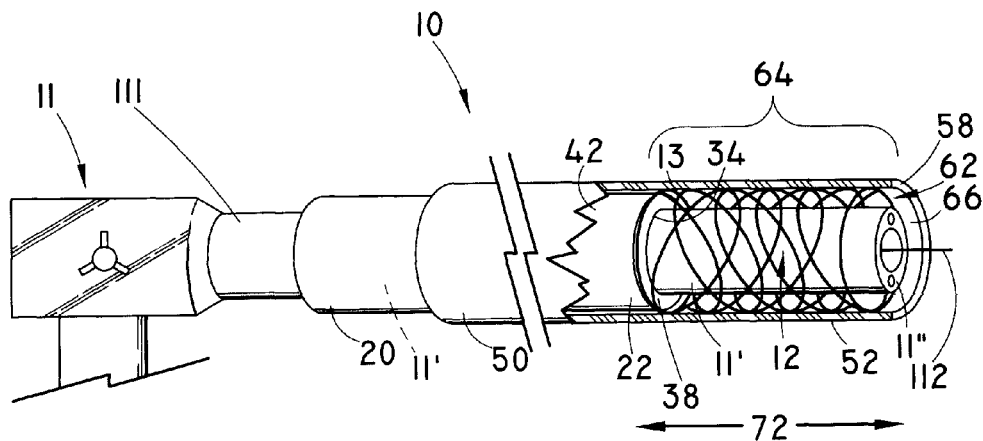
FIG. 7 provides a perspective partial view, broken away, of a medical device according to an alternative embodiment of the invention detachably engaging at least a portion of an endoscope insert.

In FIG. 7, an embodiment of the over-the-scope stent introducer 10 according to FIG. 2 is detachably mounted to an endoscope 11. FIG. 7 is similar to the embodiment of FIG. 5, but includes a stent 12 that has been placed in the outer member inner chamber 64 and at a pre-deployment position 72. In this illustrative embodiment, the stent 12 is disposed circumferentially about the endoscope insert distal end 11" and longitudinal axis 112. The pre-deployment position 72 and deployment positions 74, 76 should not be construed to include an actual stent, but should convey that, in the pre-deployment position 72 a stent would not be deploying while in a deployment position 74, 76 the stent would be deploying.

The inner member stent abutting restraint 38 (as previously described) abuts the stent proximal end 13. The insert distal end 11" is shown extending distally beyond the inner member first end portion 22 and at or near the outer member distal section opening 58. Optionally, the insert distal end 11" is proximal to the inner member stent abutting restraint 38. Alternatively, the insert distal end 11" extends distally beyond the outer member distal section opening 58, which may allow the insert distal end 11" to be positioned at the target site before the outer member distal section 52 is slid distally into place.

Figure 8:
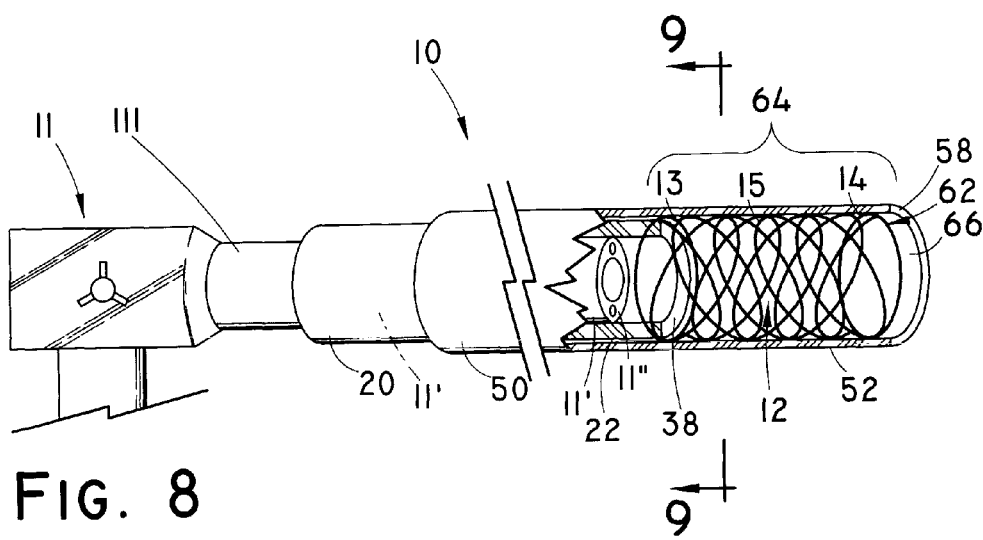
FIG. 8 provides a perspective partial view, broken away, of a medical device according to another embodiment of the invention detachably engaging at least a portion of an endoscope insert.

As illustrated in FIG. 8, the over-the-scope stent introducer 10 optionally could be detachably mounted to an endoscope 11 as described above in discussing FIG. 5 such that the insert distal end 11" is proximal to the inner member restraint 38. This arrangement may provide an advantage because the stent 12 would be within the observation field and working space of the physician's endoscope while in a radially compressed state in the outer member inner chamber 64 and during subsequent deployment. The over-the-scope stent introducer 10 further has a stent 12 contained within the outer member inner chamber 64 positioned at a pre-deployment position 72. The stent 12 may be a radially compressed self-expanding stent, a balloon expandable stent, or a non-expanding stent that is releasably contained within the outer member chamber 64. An inner member stent abutting restraint 38 abuts the stent proximal end 13.

Figure 9:
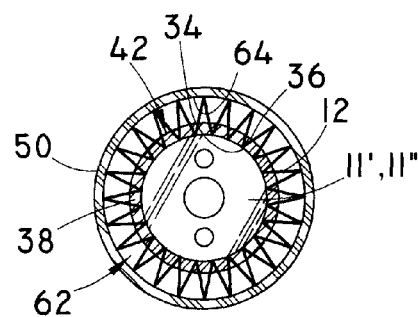
FIG. 9 is a cross sectional view of FIGS. 7 and 8 taken along the lines 9-9.

FIG. 9 shows a cross sectional end-on view of FIGS. 7 and 8 taken along the lines 9-9. This FIG. 9 includes an insert 11' (occluded by the distal end 11") having been received in the inner member channel (occupied by the insert), a portion 42 of the inner member having an inner endoscope insert engaging surface 34 and an outer surface 36. The inner member portion 42 has been inserted into the passageway 62 of the outer member 50. A stent 12 has been positioned within the outer member chamber 64. The endoscope 11 is not shown.

Figure 10A:
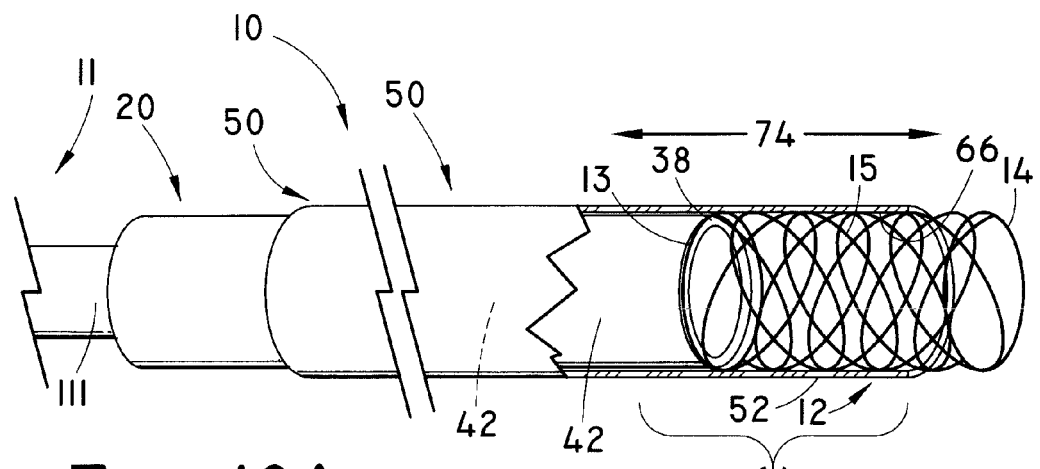
FIG. 10A provides a perspective partial view, broken away, of a medical device according to one embodiment of the invention having an elongate inner member, an elongate outer member, and a self-expanding stent in a radially compressed state in a schematically illustrative second deployment position.
Figure 10B:
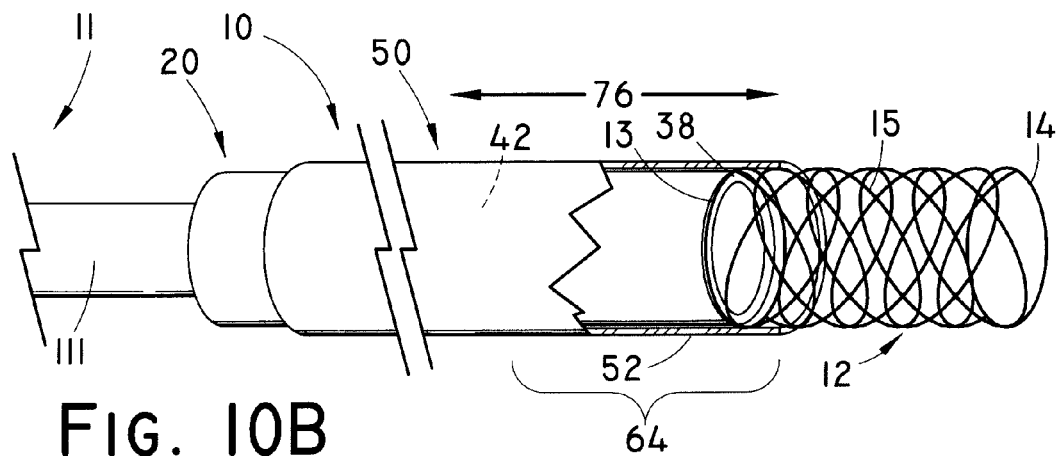
FIG. 10B is a perspective view, broken away, of FIG. 10A in another second deployment position.

FIGS. 10A and 10B show an endoscope 11 having an endoscope insert proximal section 111, and an embodiment of the over-the-scope stent introducer 10 mounted onto an endoscope insert as shown in and described above in the discussion of FIG. 5 (for clarity, the insert 11' or the distal end 11" within the inner and outer members 20, 50, respectively, are not numbered). In FIG. 10A, the distal section inner chamber 64 is positioned at a deployment position 74. A self-expanding stent distal end 14 is partially deploying into a volume exterior to the outer member distal section 52 when the distal section inner chamber 64 is positioned at said deployment position 74. In one embodiment of the invention, it should be understood that the deployment position 74 would partially deploy a balloon expandable stent and a non-expanding stent into a volume exterior to the outer member distal section 52.

In FIG. 10B, the self-expanding stent distal end 14 and intermediate portion 15 have deployed into a volume exterior to the outer member distal section 52 when the distal section inner chamber 64 is positioned at a second deployment position 76. The deployment positions include any incremental deployment stages from a deployment position 74 to a second deployment position 76 and up to and including full stent deployment that releases the stent into the vessel passageway at the target site within the patient. Thus, a third deployment position (not shown) would deploy the stend distal end 14, the intermediate portion 15, and proximal end 13 to fully deploy the stent 12 into a volume exterior to the outer member distal section.

Turning to alternative embodiments of the invention, a medical device for delivering a self-expanding stent according to the invention may be configured to extend externally of insert 11' and its working channel, while detachably engaging at or near the insert distal end 11", save for optional support bodies that detachably engage the external surface of the insert. As with the other embodiments, the insert includes a portion of the endoscope to be inserted into a patient, whether or not that portion is further shrouded with an outer sheath.

Figure 11:
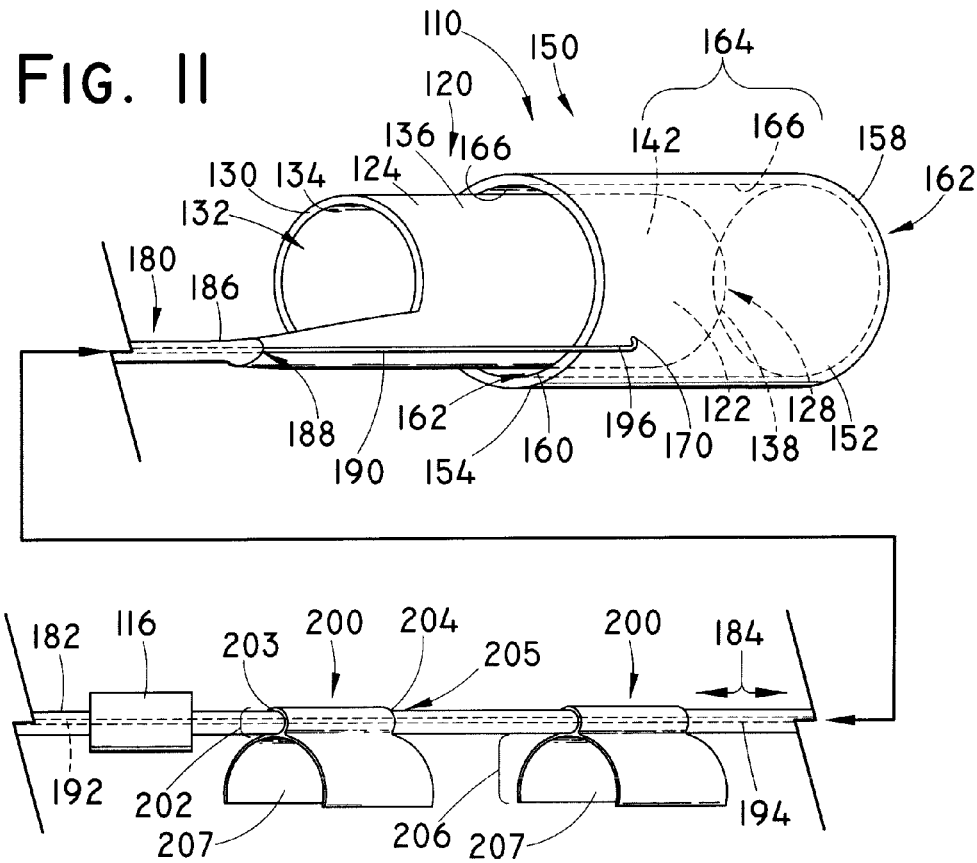
FIG. 11 provides a perspective partial view, broken away, of a medical device according to one embodiment of the invention having an inner member and an outer member.

FIG. 11 shows an over-the-scope stent introducer 110 according to one of these alternative embodiments of the invention for delivering a self-expanding stent. Like elements from the previous drawings, embodiments, and description from above are labeled the same. More particularly, the embodiment shown in FIG. 11 comprises a slideable end cap inner member 120 and a slideable end cap outer member 150. The end cap inner member 120 could be any shaft-like, rounded, oblong, circular, rectangular, square, tube-like, tubular, cylindrical, or generally rod-like structure for detachably engaging at least a portion of an endoscope insert 11'. The end cap inner member 120 and end cap outer member end cap outer member 150 typically comprise a plastic, such as injection molded plastic, polyether block amides or other thermoplastics, any suitable polymer, reinforced metal tubing, work hardened surgical stainless steel, or any conventional material with suitable properties. Furthermore, the end cap outer member end cap outer member 150 may comprise tetrafluoroethylene such as TEFLON by E.I. du Pont de Nemours and Company or other fluorine-containing resins or nylon that would not be subject to excessive stretching during axial pulling or pushing while it would be capable of being flexible with the endoscope during use. Furthermore, the construction of the end cap inner member 120 or end cap outer member end cap outer member 150 may comprise a coiled sheath, reinforced metal, or a polymer exhibiting sufficient flexibility where desired and capable of transferring tensile and/or compressive forces.

The overall length of a self-expanding stent in a compressed state or non-expanding or balloon expandable stent may vary, and so may the embodiments of the end cap inner member 120 and the end cap outer member 150. For example, the length of a present-day colonic Z-Stent® by Cook Incorporated may be offered with a length of about 4.0 cm, about 6.0 cm, about 8.0 cm, about 10.0 cm, or about 12.0 cm. An end cap inner member 120 and an end cap outer member 150 of an over-the-scope stent introducer 110 for use with these offerings should be at least as long as the stent in a compressed state if of the self-expanding variety, releasably compressed state if of the balloon expandable variety, and releasably deployable state if of the non-expanding variety. Moreover, the end cap inner member 120 and the end cap outer member 150 may be roughly equal in length, or the length of the end cap inner member 120 may be shorter or longer than the length of the end cap outer member 150, as desired. The diameter of the end cap inner member 120 and that of the end cap outer member 150, respectively, may vary as well from one embodiment to the next, depending on the type of endoscope for which the physician intends to use the over-the-scope stent introducer 110. Because the end cap inner member 120 is configured to slideably receive an endoscope insert 11', the end cap inner member 120 fits substantially concentrically over at least a portion of an endoscope insert distal end 11". Thus, the inner member inner diameter may comprise an endoscope engaging diameter of at least about 5.0 mm up to about 19.0 mm, or may be greater or less than this range at certain positions along the length of the inner member 120 given any tapering in the endoscope insert outer diameter at the insert distal end 11". Because the end cap outer member end cap outer member 150 is sized to slideably receive a portion of the end cap inner member 120, it fits substantially concentrically over the end cap inner member 120. Thus, the inner diameter of the end cap outer member 150 would be at least as great as the inner member outer diameter to accommodate slideably receiving at least a portion of the inner member 20, or from approximately 5.0 mm to approximately 19.0 mm, or may be greater or less than this range at certain positions along the length of the end cap outer member 150 given the tapering in the outer diameter of the inner member 120 or the endoscope insert distal end 11".

The end cap inner member 120 has a distal first end portion 122 and a proximal first end portion 124. The first end portion 122 and second end portion 124 include openings 128, 130, respectively, defining a channel 132 therebetween. The channel 132 may be any passageway, lumen, channel, bore, flow passage, duct, or cavity for receiving any portion of an endoscope insert distal end 11". In one embodiment of the device, the inner member channel 132 has an endoscope engaging diameter of at least about 5.0 millimeters. The channel 132 is configured to slidably receive an endoscope insert 11' such as the endoscope insert distal end 11". Also, the end cap inner member 120 may have an optional cutout portion extending from the first end distal opening 128 to the second end proximal opening 130.

Also, the end cap inner member 120 includes an outer surface 136 disposed circumferentially about the inner member 120, a stent abutting restraint 138 disposed at the first end portion 122, and an inner endoscope insert engaging surface 134. The stent abutting restraint 138 as used herein to describe any embodiments of the invention should not be construed to include the stent 12 (not shown), but is a restraint configured for limiting the proximal movement of a non-expanding, a self-expanding, and/or a balloon expandable (or combination thereof) stent 12 relative to the end cap outer member 150 during deployment. The endoscope insert engaging surface 134 of the end cap inner member 120 should not be construed to include the endoscope.

The end cap inner member 120 may be a slideable inner member or a clipping inner member depending on the engaging surface 134. In neither case should the engaging surface 134 be construed to include the endoscope, but is only used to describe an inner surface of the end cap inner member 120 configured to engage an endoscope insert distal end 11".

Turning first an end cap inner member 120 according to a slideable embodiment, the endoscope insert engaging surface 134 describes a slideably engageable surface of the inner member 120 for allowing the inner member 120 to be substantially freely slideable in at least one axial degree of freedom (except for some natural friction between abutting surfaces of the endoscope insert engaging surface 134 and the endoscope insert distal end 11") relative to an endoscope insert distal end 11". The over-the-scope stent introducer 110 according to this embodiment further includes an elongate (as already described) pushing member 180 configured to be disposed external to an endoscope insert and in communication with the end cap inner member 120. The term "communication" in describing any embodiments means any two features directly or indirectly—there may be other intermediate features—associated and capable of transferring tensile and/or compressive forces from the first feature to the second feature.

In FIG. 11, the elongate pushing member 180, by way of illustration and not by way of limitation, may be any flexible sheath or shaft having a pulling member capable of transferring tensile and/or compressive forces. Optionally, the elongate pushing member further includes a receiving passageway 188. The pushing member 180 may comprise a metal coil, polymer, polyetheretherketone ("PEEK"), reinforced metal, fiber, or plastic that is flexible but rigid enough to withstand compression so as to give the physician control over the axial movement of the end cap inner member 120 during stent deployment.

The elongate pushing member 180 further comprises a distal end 186, a flexible intermediate section 184, and a proximal end 182. The distal end 186 is in communication with the end cap inner member 120, such as with the inner member proximal first end portion 124 that in turn is in communication with the inner member first end stent abutting restraint 138. The flexible intermediate section 184 extends from the pushing member distal end 186 to the proximal end 182. The proximal end 182 may be operably associated or secured to a handle assembly 116. The handle assembly 116 is configured for the physician to hold and push to keep the inner member abutting restraint 138 from moving proximally during stent deployment, push to move the end cap inner member 120 distally for repositioning of the end cap inner member 120, or retract to move the end cap inner member 120 proximally for repositioning. Optionally, the handle assembly 116 has a pivotal handle member or actuation device. Alternatively, the handle assembly 116 may comprise a prehensile attachment associated or secured to the proximal end

182. In yet another embodiment, the handle assembly 116 may comprise a gripping surface or a grooved contour on the proximal end 182, associated, or secured to the proximal end 182.

In one embodiment, the elongate pushing member 180, together with its proximal end 182, flexible intermediate section 184, and a distal end 186 is configured to be disposed external to an endoscope insert 11' (including external to the endoscope insert distal end 11" and wherein a pulling member 190 (discussed below) is received in the pushing member passageway 188. This solves the problems of kinking, buckling, bending, and bowing that result from a pulling member 190 passing through the working channel of an endoscope and tending to kink during stent deployment. In other words, the pulling member 190 may be susceptible to kinking when it is withdrawn, because it must make a sharp turn toward the endoscope working channel. A kink in the pulling member 190 may cause difficulty during a later step where, after the stent is deployed, the end cap outer member 150 during withdrawal catches on the kink and moves the device away from the deployment site. Also, after the end cap outer member 150 is withdrawn, it may need to be reloaded with an additional stent and will then encounter the kink in the pulling member, thereby inhibiting a second use of the outer member 150. The kinking does not result when the pushing member 180 and pulling member are both disposed external to an endoscope insert 11' (including the endoscope insert distal end 11") with the pulling member disposed at least partly within the pushing member passageway 188 as taught herein.

Turning now to an end cap inner member 120 according to a clipping embodiment configured to detachably clip to an endoscope insert outer periphery 114 (e.g., the outer surface of the endoscope insert distal end 11") (see FIGS. 17A, 17B, and 17C), the endoscope insert engaging surface 134 is configured for reducing the sliding of the end cap inner member 120 relative to an endoscope insert distal end 11". The elongate pushing member 180 is optional in this embodiment.

In other words, the end cap inner member 120 has a channel 132 and an engaging surface 134 configured for receiving and dispose about at least a portion (e.g., the periphery 114) of the endoscope insert distal end 11" and, by way of example only, adapted to be capable of clamping, clutching, gripping, pinching, fastening, hooking, joining, or otherwise holding (collectively, "clipping") the periphery 114, e.g., outer surface, of the endoscope insert distal end 11". The end cap inner member 120 that is a clipping member may have an engaging surface 134 that at least partially encapsulates and detachably clips to the periphery 114 of endoscope insert distal end 11", such as with a ring structure with a segment removed therefrom, so as to permit sandwiching against endoscope insert distal end 11" in order to hold the inner member to the endoscope insert distal end 11". Alternative shapes for a clipping end cap inner member 120 include saddle, U-shaped, or Omega-shaped (horseshoe-shaped) designs that snap onto and hold the endoscope insert distal end 11". Also, the clipping end cap inner member 120 may encapsulate and hold the endoscope insert distal end 11" by friction fit. Furthermore, the engaging surface 134 may be ribbed, have a rubber coating, or have an adhesive layer so as to increase friction between these components.

The over-the-scope stent introducer 110 according to the invention also comprises an elongate end cap outer member 150 having a distal section 152 and a proximal proximal section 154. The distal section 152 and proximal section 154 include openings 158, 160, respectively, defining a passageway 162. The passageway 162 may be any passageway, lumen, channel, bore, flow passage, duct, or cavity sized to slideably receive at least a portion 142 of the end cap inner member 120.

Also, the end cap outer member 150 includes a stent carrying inner chamber 164 disposed in the passageway 162 at the outer member distal section 152. As a result, the end cap outer member 150 is substantially concentric to the end cap inner member 120 and axially slideable over the inner member received portion 142 outer surface 136 disposed circumferentially about the inner member 120. The inner chamber 164 may be any volume along a portion of the length of the passageway 162 within the distal section that is configured to releasably constrain a radially compressed self-expanding, a balloon expandable stent, or a non-expanding stent such as a plastic tube that stays in the patient at a target site because the outer diameter is sufficiently larger than the vessel passageway such as to stretch the vessel and thereby stay in place due to the vessel's elastic radially compressive forces. The chamber as used herein to describe any embodiments of the invention should not be construed to include the stent, but is a cavity within the distal section 152 comprising a restraint, such as an inner surface 166 of the end cap outer member 150, configured for releasably constraining a radially compressed self-expanding stent. In one embodiment of the invention, the over-the-scope stent introducer 110 further comprises a radially compressed self-expanding stent, a balloon expandable stent, or a non-expanding stent in the inner chamber 164.

Figure 12:
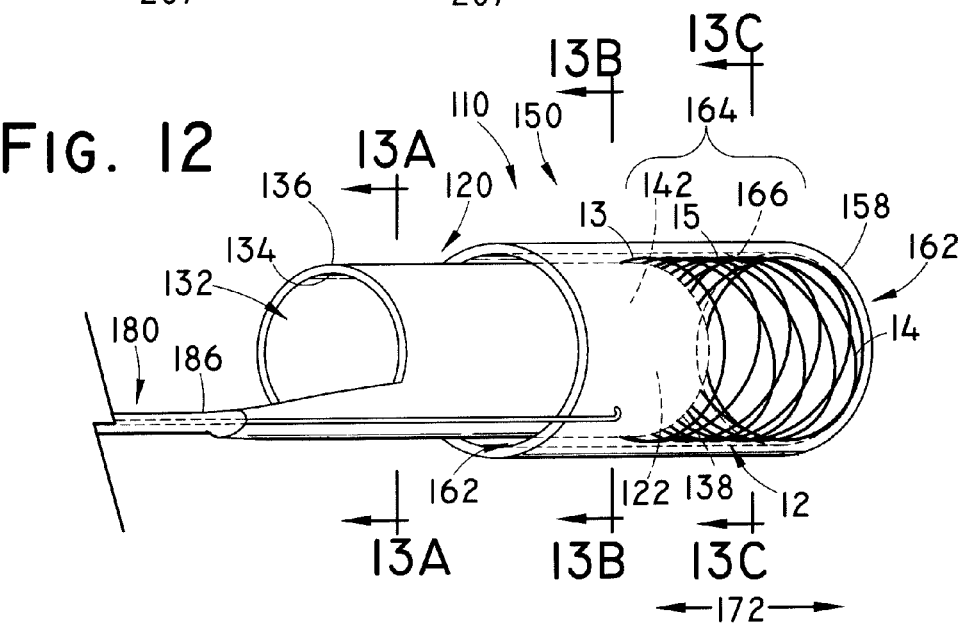
FIG. 12 provides a perspective partial view, broken away, of a medical device according to an embodiment of the invention having an inner member, an outer member, and a self-expanding stent in a radially compressed state in a schematically illustrative pre-deployment position.
Figure 15A:
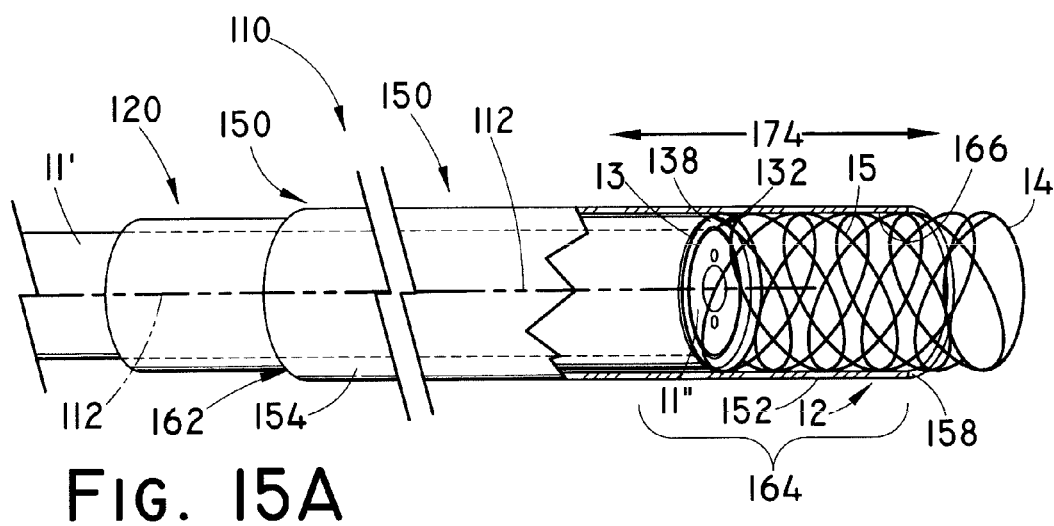
FIG. 15A provides a perspective partial sectional side view, broken away, of a medical device according to another embodiment of the invention detachably engaging at least a portion of an endoscope insert and in a schematically illustrative second deployment position.
Figure 15B:
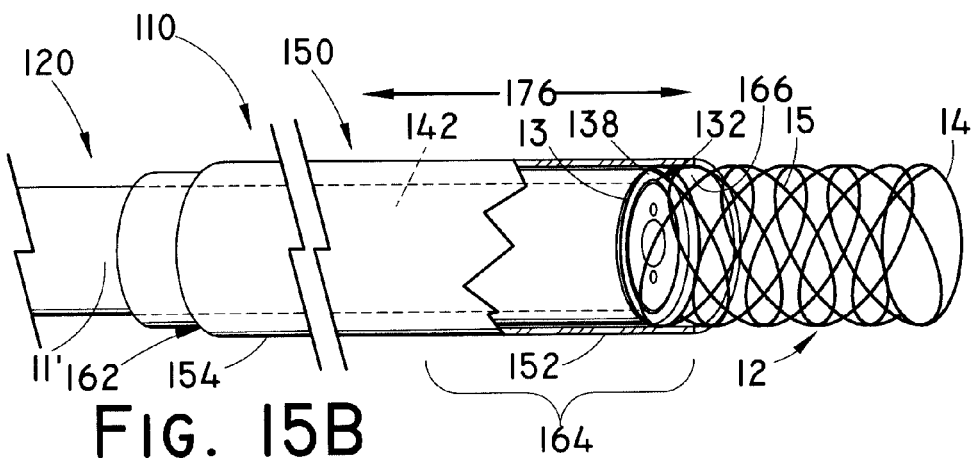
FIG. 15B is a perspective view partial sectional side view, broken away, of FIG. 15A in another second deployment position.

The end cap outer member 150 is axially slideable relative to the inner member portion outer surface 136 between a pre-deployment position 172 and a deployment position 174, 176, as shown in FIGS. 12, 15A, and 15B. The pre-deployment position 172 and deployment positions 174, 176 should not be construed to include an actual stent, but should convey the meaning that, in the pre-deployment position 172 a stent would not be deploying while in a deployment position 174, 176 the stent would be deploying. The deployment positions include any incremental deployment stages from a pre-deployment position 172 to a deployment position 174 and/or to a second deployment position 176 up to and including full stent deployment that releases the stent into the vessel passageway at the target site within the patient.

As shown in FIG. 11, one embodiment of the over-the-scope stent introducer 110 further comprises an elongate pulling member 190 configured to move the outer member 150 proximally over the inner member distal first end portion 122. The pulling member 190 is in communication—directly or indirectly—with an end cap outer member 150 pulling member link body 170 for moving the outer member between a predeployment position 172 and a deployment position 174, 176. The pulling member 190 may be metallic wire, stainless steel, nickel titanium alloy, or other alloy, or non-metallic cord. Other examples include a monofilament wire, suture, steel cable, or textile cord that is twisted (wound) or braided. The pulling member 190 has a proximal retractor end 192, a flexible intermediate portion 194 slideably received in the pushing member passageway 188, and a distal connecting end 196 secured to the outer member pulling member link body 170. In one embodiment, the elongate pulling member 190 is configured to be slideably received in the pushing member passageway 188 such that both the pulling member 190 and pushing member 180 are configured to be disposed external to an endoscope insert 11' such as the endoscope insert distal end 11", with the pulling member 190 disposed at least partly within the pushing member passageway 188.

Certain non-limiting examples of an outer member pulling member link body 170 include any receptor such as a slot, recess, hole, cutout, or aperture. Other non-limiting examples of a outer member pulling member link body 170 include a securing mechanism such as a pin, shaft, thread, rod, bar, nut, bolt, screw, cotter and pin, or other linkages for receiving a secured arrangement with the elongate pulling member distal connecting end 196. Certain non-limiting examples of a distal connecting end 196 include a tying structure that ties to the pulling member link body in the case of a securing mechanism, or in the case of a link body that is a receptor, the distal connecting end 196 may be a mushroom-shaped structure or a hooking structure such as a J-hook or an S-hook, which then fit into the receptor. The pulling member proximal retractor end 192 may be disposed for gripping by the physician, or may be operably in communication with any handle as previously described.

As shown in FIG. 11, the over-the-scope stent introducer 110 may further comprise one or more optional support bodies 200. A support body 200 has a guide portion 202 and a base 206. The guide portion 202 has a proximal opening 203 and a distal opening 204 defining a passageway 205 that slidably receives a portion of the elongate pushing member 180, the elongate pulling member 190, and/or an accessory channel containing either the pushing member 180 or pulling member 190. As used to describe an embodiment of the support body 200, the term "passageway" is understood to be any lumen, chamber, channel, opening, bore, aperture, orifice, flow passage, passageway, or cavity configured to facilitate the sliding of another component, such as a pushing member 180, pulling member 190, and/or accessory channel.

The support body 200 further comprises a base 206 having an endoscope engaging surface 207. In either the case of a slideable or clipping embodiment of the inner member 120, the support body endoscope engaging surface 207 may be slideable or clippable relative to the endoscope. The optional support body 200 is generally adapted to be capable of bridging or otherwise connecting the elongate pushing member 180 (where optionally utilized or the elongate pulling member 190 where the pushing member 180 is not utilized, or some other accessory channel member containing either the pushing member 180 or pulling member 190) to the endoscope insert 11'. In one embodiment, the support body 200 operatively couples the over-the-scope stent introducer 110 and the endoscope insert 11' by a support body endoscope engaging surface 207 that clips to the endoscope insert proximal section 111, and in another embodiment medical grade tape operatively couples the support body 200 and/or the pushing member proximal end 182 to the endoscope insert proximal section 111. Optionally, the pushing member proximal end 182 may detachably mount to an endoscope 11 and/or the endoscope insert proximal section 111 by one of the embodiments of optional latching members 230, 240, 250, 260 shown in FIGS. 1A, 1B, 1C, 1D, 1E, 1F, 1G, and 1H or latches, screws, clamps, cams, hooks, sleeves, collets, and the like.

FIG. 12 shows an over-the-scope stent introducer 110 for delivering a stent 12 comprising an end cap inner member 120 and an end cap outer member 150 as previously described in connection with FIG. 11. A stent 12 has proximal and distal ends 13, 14, respectively, and an intermediate portion 15 is radially compressed in the outer member chamber 164. A stent abutting restraint 138 disposed at the inner member first end portion 122 abuts the stent proximal end 13. Once a stent (e.g., a self-expanding stent in a radially compressed state, a balloon expandable stent, or a non-expanding stent) is loaded by any conventional means in a radially compressed state within the end cap outer member chamber 164 of the over-the-scope stent introducer 110, the inner member stent abutting restraint 138 is configured to control proximal axial movement of a stent 12 relative to the inner member 120. In one embodiment, the restraint 138 is sized to be large enough to make sufficient contact with the loaded proximal end 13 of the stent 12. For example, the restraint 138 may be the circumferential wall thickness of the inner member first end portion 122 (e.g., distal end face of the inner member first end portion 22) for abutting against the stent proximal end 13, or the restraint 138 may be any protuberance, protrusion, bulge, bow, convex, bump, knob, raising, lump, or combination thereof for abutting against the stent proximal end 13. In addition to helping to stop the stent's proximal movement in a non-deployed state, the restraint 138 helps to "push" a stent 12 out of the chamber 164 by preventing the stent from migrating proximally when the end cap outer member 150 retracts proximally relative to the inner member 120 to deploy the stent 12. Optionally, the restraint 138 may be radiopaque so as to aid in positioning stent 12 within the target site.

Figure 13A:
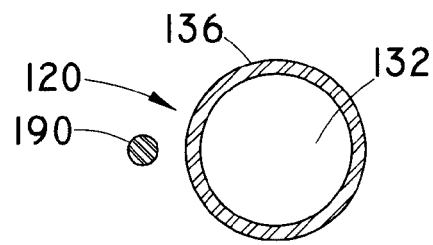
FIG. 13A is a cross sectional view of FIG. 12 taken along the lines 13A-13A.

FIG. 13A shows a cross sectional view of FIG. 12 taken along the lines 13A-13A. This Figure includes the inner member 120 and its channel 132. Optionally, the inner member channel 132 may detachably mount to an endoscope 11 (not shown in FIGS. 13A, 13B, and 13C). Also shown is an elongate pulling member 190 alongside the inner member 120. Although shown spaced from an inner member outer surface 136 and exterior to the inner member, the pulling member 190 optionally may abut the outer surface 136. For clarity, other proximal components of the embodiment are not shown.

Figure 13B:
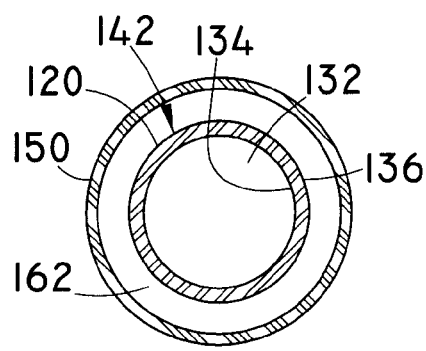
FIG. 13B is a cross sectional view of FIG. 12 taken along the lines 13B-13B.

FIG. 13B shows a cross sectional view of FIG. 12 taken along the lines 13B-13B. This Figure includes a portion 142 of the end cap inner member 120 having an inner member channel 132, inner endoscope insert engaging surface 134, and an outer surface 136. The inner member portion 142 is shown inserted into (e.g., received within) the passageway 162 of the end cap outer member 150, the outer member 150 being substantially concentric to the inner member 120 and axially slideable over the inner member portion outer surface 136. For clarity, other proximal components of the embodiment are not shown.

Figure 13C:
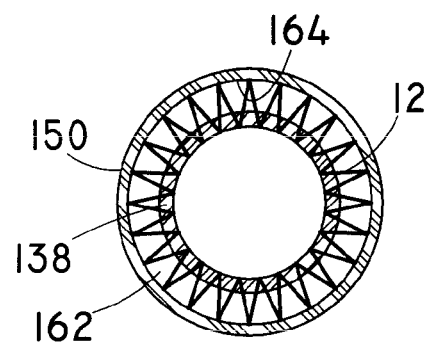
FIG. 13C is a cross sectional view of FIG. 12 taken along the lines 13C-13C.

FIG. 13C shows a cross sectional view of FIG. 12 taken along the lines 13C-13C. The Figure includes an end-on view to show the inner member stent abutting restraint 138, an end cap outer member 150, and the stent 12 releasably contained within the outer member chamber 164. The inner chamber 164 is disposed in the passageway 162 of the outer member distal section and configured to releasably contain the stent 12. For clarity, other proximal components of the embodiment are not shown.

Figure 14:
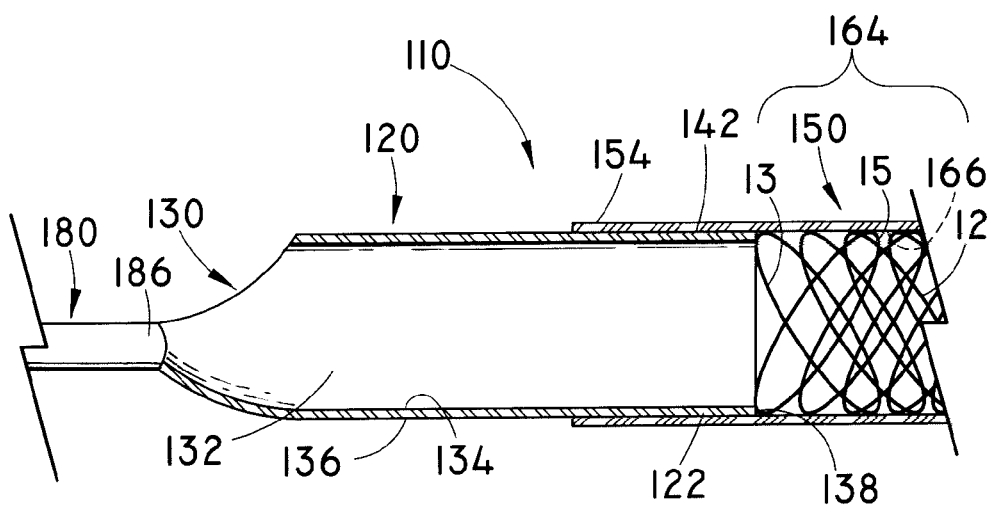
FIG. 14 a partial sectional side view, broken away, of FIG. 12.

FIG. 14 depicts a partial side sectional view of FIG. 12 taken lengthwise as previously described in connection with FIG. 11. In FIG. 14, a stent 12 comprising a proximal end 13 and an intermediate portion 15 are shown releasably contained within the end cap stent carrying inner chamber 164, with the inner member restraint 138 abutting the stent proximal end 13. The end cap outer member proximal section 154 has slideably received at least a portion 142 of the end cap inner member 120. The inner member 120 includes an outer surface 136 that may be in slideable contact with the outer member inner surface 166 at or near its inner member first end portion 122. A proximal opening 130 is disposed at the inner member channel 132, both of which are configured to receive an endoscope insert distal end 11" (not shown). The inner member 120 further has an inner endoscope insert engaging surface 134. Also shown is an optional non-sectioned view of an elongate pushing member 180 (an elongate pulling member 190 omitted for clarity), which may be omitted in the case of a clipping inner member 120 as previously described.

FIGS. 15A and 15B show partial side sectional views of an embodiment of the invention as described in connection with FIG. 11 and comprising an elongate endoscope insert having an insert distal end 11'' and an insert proximal section, the insert distal end 11'' comprising a longitudinal axis 112 as previously described. The end cap inner member 120 has been detachably mounted onto the endoscope insert distal end 11'' disposed in the inner member channel 132 at a position proximal to the inner member restraint 138 and to the stent proximal end 13. The outer member proximal section 154 has slideably received within its passageway 162 at least a portion 142 of the inner member 120.

Also shown is a self-expanding stent distal end 14 being radially compressed within a chamber 164 positioned at the end cap outer member distal section 152 of the over-the-scope stent introducer 110, although the stent could also be a non-expanding stent, a balloon expandable stent, or a combination of these types of stents. Again, stent is used to describe an embodiment of a self-expanding, balloon expandable, and non-expanding implantable medical devices, such as a stent, prosthetic venous valve, and other prosthetic articles for placement inside a patient's body.

FIGS. 15A and 15B also show stent deployment positions 174, 176 in which the stent would be deploying from the over-the-scope stent introducer 110. The deployment positions include any incremental deployment stages from a pre-deployment position 172 (see FIG. 12 for example) to a deployment position 174 (see FIG. 15A for example) and/or to a second deployment position 176 (see FIG. 15B for example) up to and including full stent deployment that releases the stent into a volume exterior to the outer member distal section 152 (e.g., the vessel passageway at the target site within the patient). By way of example only and not by way of limitation, in FIG. 15A the deployment position 174 comprises deploying stent distal end 14 into a volume exterior to the outer member distal section 152. In FIG. 15B, the end cap outer member 150 is shown in another second deployment position 176 relative to the inner member distal first end portion 122 and/or restraint 138. In FIG. 15B by way of example and not by way of limitation, the outer member proximal section 154 is proximal to the position of the outer member proximal section 154 of FIG. 15A, thereby resulting in the self-expanding stent distal end 14 and some of the intermediate portion 15 deploying into a volume exterior to the outer member distal section 152.

Figure 16:
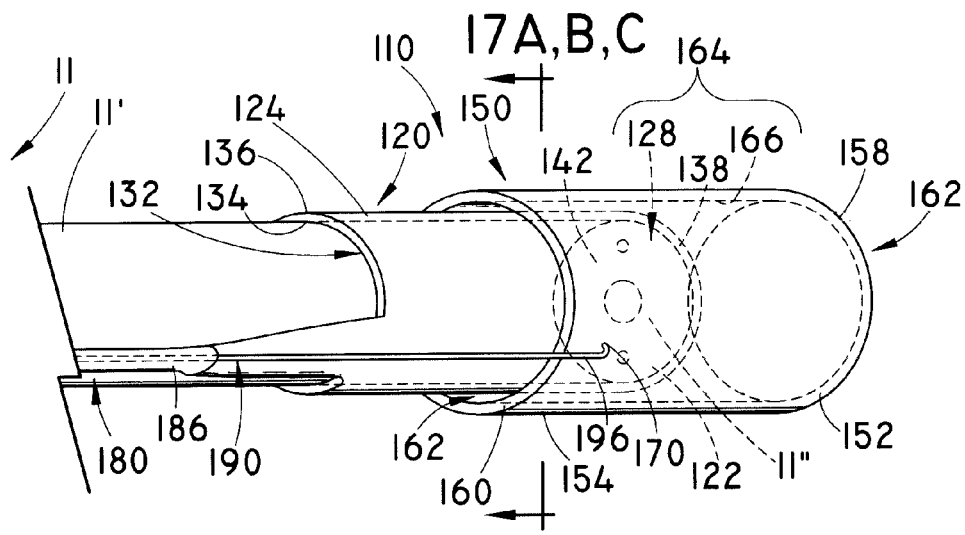
FIG. 16 provides a perspective partial view of a medical device according to an alternative embodiment of the invention detachably engaging at least a portion of an endoscope insert.

FIG. 16 shows an embodiment of the over-the-scope stent introducer 110 as described in connection with FIG. 11 detachably mounted to an endoscope insert distal end 11'' while the end cap outer member 150 is substantially concentric to the end cap inner member 120 and axially slideable over the inner member received portion 142 outer surface 136 disposed circumferentially about the inner member 120. The insert 11' has been positioned in a slideable or a clipping inner member 120 by placement within the inner member channel 132. The inner endoscope insert engaging surface 134 detachably engages a portion 142' of the insert distal end 11''. While the insert distal end 11'' is shown proximal to the inner member first end portion 122 and the inner member restraint 138, the insert distal end 11'' could also extend distally beyond the inner member first end portion 122, and may even extend to, near, or distally beyond the outer member distal section 152 or distal section opening 158. Also shown is an optional elongate pushing member 180, which may be omitted in the case of a clipping inner member 120 as previously described.

Figure 17A:
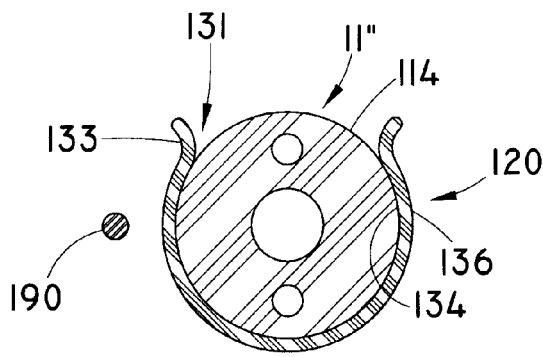
FIGS. 17A, 17B, and 17C are cross sectional views of FIG. 16 taken along the lines 17A-17A, 17B-17B, and 17C-17C of alternative embodiments of an inner member detachably engaging a portion of an endoscope insert according to the invention.
Figure 17B:
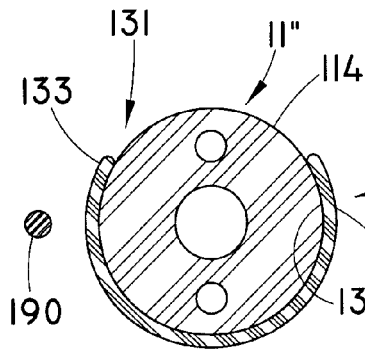
Figure 17C:
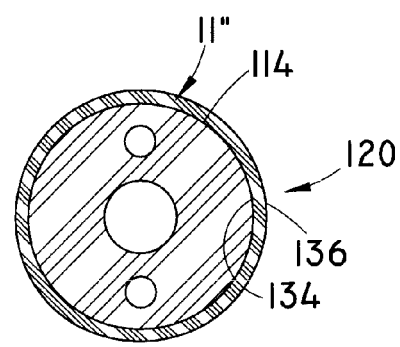

FIGS. 17A, 17B, and 17C are end-on views taken along lines 17A-17A, 17B-17B, and 17C-17C of FIG. 16 of various embodiments of the end cap inner member 120 according to the invention, whether of the clipping or slideable type of inner member 120, and shown detachably mounted to an endoscope insert distal end 11''. The inner member 120 has a channel 132 and an endoscope insert engaging surface 134 configured for receiving at least a portion of the endoscope insert distal end 11'' and, by way of example, adapted to be clipping or slideable relative to the periphery or outer surface of the endoscope insert distal end 11''. As shown in FIGS. 17A and 17B, the inner member 120 may have an engaging surface 134 that at least partially encapsulates the endoscope insert distal end 11'', such as a ring structure with a cutout 131 for at least partially enclosing in a slideable or clipping configuration against endoscope insert distal end 11''. Alternative shapes for an inner member 120 having a cutout 131 include saddle, U-shaped, or Omega-shaped (horseshoe-shaped) designs.

As shown in FIGS. 17A, 17B, 18A, and 18B, the end cap inner member 120 and the end cap outer member 150 optionally comprise alignment elements 131, 133, 161, 163. In one embodiment, the inner member alignment element 133 comprises a guide track, which may be substantially bent as shown illustratively in FIG. 17A or substantially straight as in FIG. 17B, and configured for slideable communication with an outer member alignment element 163 comprises a groove of the outer member 150 as shown in FIGS. 18A and 18B. Also, the inner member 120 may encapsulate the endoscope insert distal end 11'' as shown in FIG. 17C. Also shown in FIGS. 17A, 17B, and 17C spaced from an outer surface 136 of, and exterior to, the inner member 120 is the pulling member 190, which optionally may abut the outer surface 136. For clarity, other proximal components of the embodiment are not shown.

FIGS. 18A and 18B show partial views, broken way, of end cap outer members 150 according to embodiments of the invention, including a distal section 152 for slideably receiving a portion of the inner member 120 within a portion of the outer member passageway 162. The end cap outer member 150 of FIGS. 18A and 18B optionally includes an alignment element 161 that is an outer member track for slideably engaging and detachably engaging an alignment element 131 that is a cutout of the inner member 120 and/or an optional alignment element 163 that is a groove for slideably engaging and detachably engaging the alignment element 133 that is a guide track of the inner member 120 of FIGS. 17A and 17B, respectively. This arrangement facilitates proper alignment of the inner member 120 and the end cap outer member 150, which may otherwise rotate or shift during navigation and positioning of the delivery system during placement inside the patient's body or during deployment of the stent as the end cap outer member 150 retracts proximally from the relative position of the inner member 120 to expose and to deploy the stent 12. The tracked alignment element 161 and grooved alignment element 163 are shown extending to the distal section opening 158 and may also extend to the proximal second end opening 160 (not shown). The outer member 150 in FIG. 18C has more of uniform distal section opening 158 and passageway 162, and may be used with the inner member 120 of FIG. 17C or the alternative embodiments shown or described in connection with FIGS. 17A and 17B.

Figure 19A:
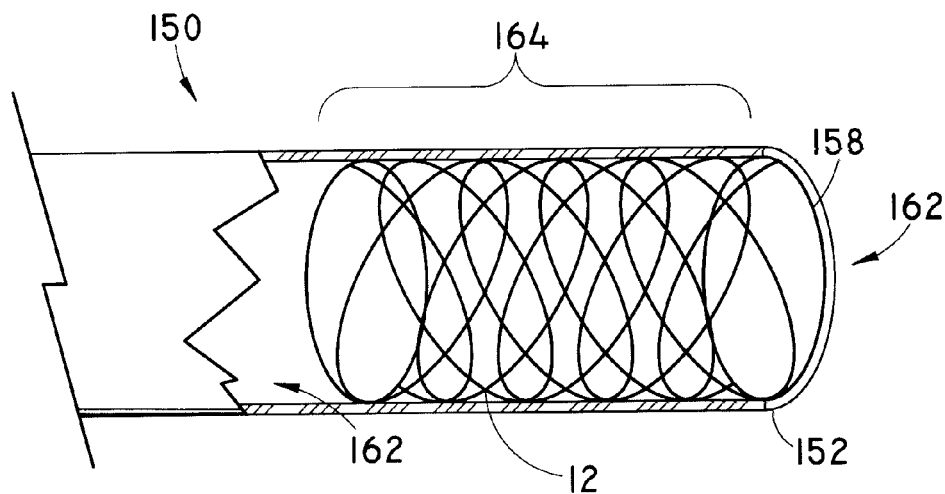
FIG. 19A provides a perspective partial view of an alternative embodiment of an outer member according to the invention and containing a schematically illustrative self-expanding stent in a radially compressed state.

FIG. 19A shows a schematic representation of an end cap outer member 150 having a chamber 164 containing a stent 12. As a schematic representation, FIG. 19A represents an end cap outer member 150 of FIGS. 18A, 18B, 18C, and other outer members consistent with the description of an end cap outer member 150 according to the embodiments of FIGS. 11, 12, 13C, and 14-16 being substantially concentric to the inner member 120. The end cap outer member 150 of FIG.

Figure 19B:
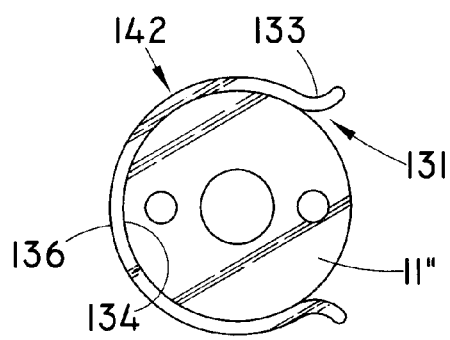
FIGS. 19B, 19C, and 19D are perspective partial end views of alternative embodiments of an inner member according to the invention.
Figure 19C:
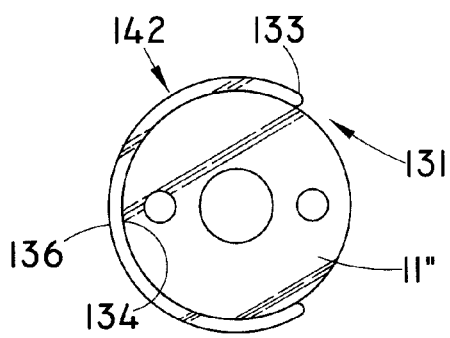
Figure 19D:
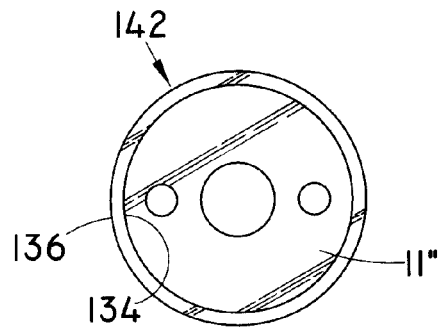

19A has a passageway 162 sized to slideably receive at least an inner member portion 142 schematically represented in the end-on views of FIGS. 19B, 19C, 19D, and other inner members consistent with the description of an inner member 120 according to the embodiments of FIGS. 11-13B, and 14-17C that are configured to slideably receive an endoscope insert. Though FIGS. 19B, 19C, and 19D are illustrated with an endoscope insert distal end 11", they could equally be illustrated without the endoscope insert distal end 11". Furthermore, the end cap outer member 150 could receive the inner member portion 142 before or after the inner member 120 receives the endoscope insert distal end 11".

Methods

Figure 20:
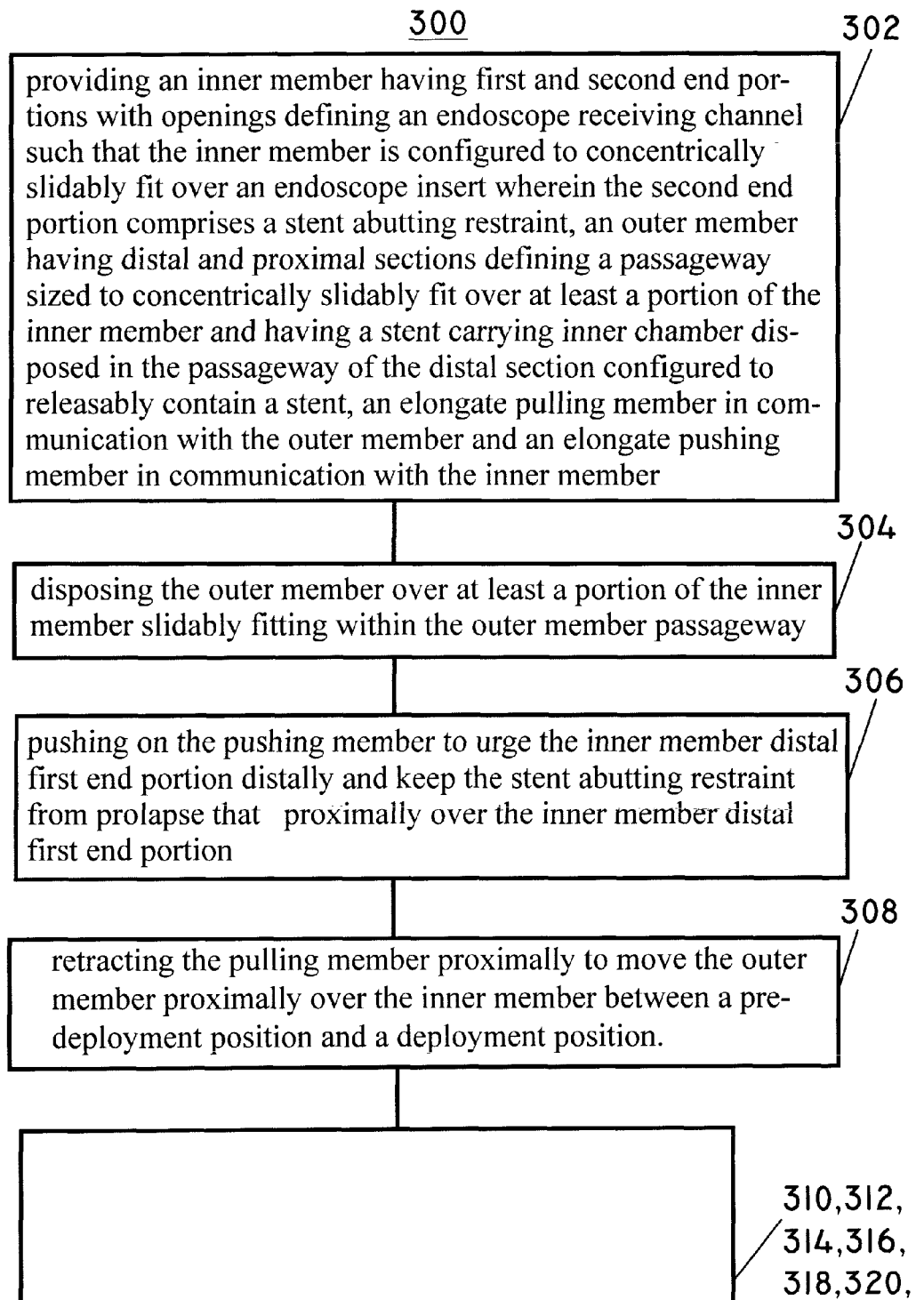
FIG. 20 is a block diagram illustrating a method of the invention.

Methods of using an over-the-scope stent introducer 10, 110 for delivering a stent 12 are also provided. FIG. 20 shows one embodiment of the method 300 according to the invention.

For example, a method 300 according to the invention includes the step of providing (step 302) an inner member 20, 120 having a first end portion 22, 122 with an opening 28, 128 and a second end portion 24, 124 with openings 30, 130 defining an endoscope receiving channel 32, 132 such that the inner member is configured to concentrically slidably fit over an endoscope insert 11 wherein the second end portion comprises a stent abutting restraint 38, 138, an outer member 50, 150 having a distal section 52, 152 with an opening 58, 158 and a proximal section 54, 154 with an opening 60, 160 defining a passageway 62, 162 sized to concentrically slidably fit over at least a portion 42, 142 of the inner member and having a stent carrying inner chamber 64, 164 disposed in the passageway of the distal section configured to releasably contain a stent 12, an elongate pulling member 70, 190 in communication with the outer member and an elongate pushing member 40, 180 in communication with the inner member.

Another step comprises disposing (step 304) the outer member over at least a portion of the inner member slidably fitting within the outer member passageway.

Pushing (step 306) on the pushing member urges the inner member distal first end portion distally. This has the result of keeping the stent (or a stent-carrying outer member or endoscope insert) from prolapsing proximally with the withdrawing of the outer member. As will be understood, "pushing" on the pushing member will keep the inner member distal first end portion and its stent abutting restraint (and therefore the stent 12) from translating as a result of an outer member being pulled proximally over the stent during stent deployment; thereby "pushing" holds the stent in place at the desired deployment site within the patient's body.

Retracting (step 308) the pulling member proximally moves the outer member proximally over the inner member between a pre-deployment 72, 172 position and a deployment position 74, 76, 174, 176.

The method 300 further comprises the step of lubricating (step 310) the outer member. If done before insertion into the patient, a lubricated outer member facilitates advancing the outer member, and therefore the inner member and endoscope insert, through the tortuous path of vessel passageways.

The stent 12 may be preloaded (step 312) within the outer member stent carrying inner chamber 64, 164 disposed in the passageway of the outer member distal section. A stent 12 comprises proximal and distal ends 13, 14, respectively, and an intermediate portion 15. The stent proximal end 13 is restrained from proximal movement by the stent abutting restraint 38, 138 of the inner member.

An endoscope 11 is provided (step 314). The endoscope comprises an elongate endoscope insert 11' having an insert distal end 11" and an insert proximal section 111, the insert distal end 11" comprises a longitudinal axis 112. As used herein and throughout to describe embodiments of the invention, the term "longitudinal axis" should be considered to be an approximate lengthwise axis, which may be straight or may at times even be curved because the endoscope insert 11' is flexible or partially flexible.

In one embodiment, the stent 12 is loaded (step 316) within the outer member chamber 64, 164 such that it is circumferentially disposed about the endoscope insert distal end 11" and longitudinal axis.

In another step, at least the endoscope insert distal end 11" is inserted (step 318) within the inner member channel 32, 132.

In one embodiment, the endoscope insert distal end 11" is advanced (step 320) through the anus and rectum and colon to a target site for stent deployment within a patient. This includes advancing (step 320) the endoscope insert distal end 11" through the sigmoid colon, descending colon, ascending colon, transverse colon, pylorus, and/or into the cecum or advanced by the colonoscopist elsewhere in the gastrointestinal tract of a patient's body.

In one embodiment of the over-the-scope stent introducer 10, 110 provided (step 302), the elongate pushing member 180 is disposed (step 322) external to the endoscope insert 11', the pushing member having a pulling member receiving passageway 188, and the elongate pulling member inserted (step 324) within the pushing member passageway such the pulling and pushing members are disposed external to an endoscope insert (i.e., not disposed within the working channel of the endoscope), with the pulling member disposed at least partly within the pushing member passageway.

In another step, the outer member and the inner member are detachably operatively coupled (step 326). For instance, they may be coupled by alignment elements 131, 133, 161, 163 or by latch members 230, 240, 250, 260.

A method of providing a medical device for delivering a stent as described above need not be performed sequentially. For instance, a stent may be preloaded (312) within the outer member stent carrying inner chamber 64, 164, and then the over-the-scope stent introducer 10, 110 provided (step 302). Also, the outer member may be disposed (step 304) over the inner member before or after the over-the-scope stent introducer 10, 110 provided (step 302). Furthermore, the endoscope 11 may be provided (step 314) before the over-the-scope stent introducer 10, 110 provided (step 302). Indeed, the inner member and outer member may be operatively coupled (step 326) before or after the endoscope insert distal end 11" is inserted (step 318) within the inner member channel 32, 132. These are only a few illustrative and non-limiting examples showing that the method 300 need not be performed sequentially.

It is intended that the foregoing detailed description of the medical devices and methods be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

The foregoing disclosure includes the best mode devised by the inventor for practicing the invention. While particular elements, embodiments and applications of the present invention have been shown and described, it will be understood, of course, that the invention is not limited thereto since modifications may be made by those skilled in the art, particularly in light of the foregoing teachings. It is apparent, however, that several variations in accordance with the present invention may be conceivable by one skilled in the art. Therefore, it is contemplated that the appended claims should be construed to include such modifications and to cover such modifications and incorporate those features that come within the spirit and scope of the invention.

What is claimed is:

1. A method of using an over-the-scope stent introducer, comprising the steps of:
    providing a stent having a proximal end and a distal end;
    providing an endoscope having an endoscope insert comprising an insert distal end and an external surface;
    providing an inner member external to the endoscope insert, the inner member comprising an outer surface and further comprising a distal first end portion and a proximal second end portion, the portions having openings defining an endoscope insert receiving channel comprising an endoscope insert engaging surface that is configured to slideably fit over at least the external surface of the endoscope insert distal end, wherein the distal first end portion of the inner member comprises a distal stent abutting restraint having a thickness configured to control proximal axial movement of the stent, the proximal end of the stent positioned distal to the inner member so that the distal stent abutting restraint operably contacts the proximal end of the stent;
    providing an outer member external to the inner member, the outer member having distal and proximal sections defining a passageway sized to slideably fit over at least a portion of the inner member outer surface and having a stent carrying inner chamber disposed in the passageway of the distal section and configured to releasably contain the stent;
    providing a pushing member external to a portion of the endoscope insert and in communication with the inner member first end portion, the pushing member being configured to prevent proximal movement of the stent relative to the outer member as the stent carrying inner chamber of the outer member is being pulled proximally over the inner member distal first end portion;
    providing a pulling member in communication with the outer member distal section, the pulling member being configured to move the stent carrying inner chamber of the outer member proximally and telescopically over the inner member between a pre-deployment and deployment position in order to deliver the stent;
    disposing the inner member slideably over at least a portion of the endoscope insert distal end being received in the endoscope receiving channel of the inner member; and
    disposing the outer member slideably over at least the portion of the inner member fitting within the outer member passageway.

2. The method of claim 1 further comprising the step of lubricating the outer member.

3. The method of claim 1 further comprising the step of preloading the stent within the outer member stent carrying inner chamber and restraining the stent from proximal movement by the stent abutting restraint of the inner member.

4. The method of claim 1 wherein the step of providing the endoscope comprises providing the endoscope with an elongate endoscope insert, and an insert proximal section, the insert distal end having a longitudinal axis.

5. The method of claim 4 further comprising the step of loading a stent circumferentially about the endoscope insert distal end and longitudinal axis.

6. The method of claim 4 further comprising the step of inserting the elongate endoscope insert within the inner member channel.

7. The method of claim 4 further comprising the steps of advancing the endoscope insert distal end through the anus and rectum and colon to a target site for stent deployment within a patient.

8. The method of claim 1 wherein the step of providing the pushing member comprises the step of providing an elongate pushing member having a distal end in communication with the inner member and having a pulling member receiving passageway, wherein the pushing member is positioned alongside the endoscope insert.

9. The method of claim 8 wherein the step of providing the pulling member comprises the step of providing an elongate pulling member having a distal connecting end secured to the outer member, wherein the pulling member is positioned alongside the endoscope insert.

10. The method of claim 9 further comprising the step of inserting the elongate pulling member within the pushing member passageway such that the pulling and pushing members are disposed external to the endoscope insert, with the pulling member disposed at least partly within the pushing member passageway.

11. The method of claim 10 further comprising the steps of retracting the elongate pulling member, resulting in the moving of the outer member proximally and telescopically over the inner member distal first end portion between the pre-deployment position and the deployment position, and further resulting in deploying the stent.

12. The method of claim 1 further comprising the step of detachably operatively coupling the outer member and the inner member.

13. The method of claim 1 further comprising the step of pushing on the pushing member to urge the inner member distal first end portion distally and keep the stent abutting restraint from prolapse that might result from the outer member being pulled proximally over the inner member distal first end portion.

14. The method of claim 1 further comprising the step of retracting the pulling member proximally to move the outer member proximally over the inner member between the pre-deployment position and the deployment position.

15. The method of claim 14 further comprising the step of deploying the stent.

* * * * *